United States Patent
Lim et al.

(10) Patent No.: US 10,548,557 B2
(45) Date of Patent: Feb. 4, 2020

(54) X-RAY APPARATUS AND X-RAY IMAGING METHOD

(71) Applicant: Samsung Electronics Co., Ltd., Suwon-si, Gyeonggi-do (KR)

(72) Inventors: Jae-guyn Lim, Seongnam-si (KR); Seong-deok Lee, Seongnam-si (KR); Sung-ho Chang, Hwaseong-si (KR); Min-hyung Chung, Seoul (KR); Woo-sup Han, Yongin-si (KR); Eung-bum Kim, Hwaseong-si (KR); Woo-young Jang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1033 days.

(21) Appl. No.: 14/884,269

(22) Filed: Oct. 15, 2015

(65) Prior Publication Data

US 2016/0106389 A1  Apr. 21, 2016

Related U.S. Application Data

(60) Provisional application No. 62/064,707, filed on Oct. 16, 2014.

(30) Foreign Application Priority Data

Nov. 14, 2014  (KR) .................. 10-2014-0158911

(51) Int. Cl.
  *A61B 6/00*  (2006.01)
(52) U.S. Cl.
  CPC ............... *A61B 6/54* (2013.01); *A61B 6/487* (2013.01); *A61B 6/504* (2013.01); *A61B 6/541* (2013.01)

(58) Field of Classification Search
  CPC ......... A61B 6/487; A61B 6/504; A61B 6/527; A61B 6/54; A61B 6/541
  See application file for complete search history.

(56) References Cited

U.S. PATENT DOCUMENTS

| | | |
|---|---|---|
| 5,119,409 A | 6/1992 | Nields et al. |
| 5,917,883 A | 6/1999 | Khutoryansky et al. |
| 7,239,685 B2 | 7/2007 | Petrick et al. |
| 7,496,175 B2 | 2/2009 | Sakaguchi et al. |

(Continued)

FOREIGN PATENT DOCUMENTS

| | | |
|---|---|---|
| CN | 1526360 | 9/2004 |
| CN | 101330872 | 12/2008 |

(Continued)

OTHER PUBLICATIONS

European Supplementary Partial Search Report (Communication pursuant to Rule 164(1) EPC) in Application No. 15850258.3 dated Oct. 23, 2017 (10 pages).

(Continued)

*Primary Examiner* — Dani Fox
(74) *Attorney, Agent, or Firm* — Staas & Halsey LLP

(57) ABSTRACT

An X-ray apparatus includes a controller controlling generation of an X-ray and adjusting at least one of a plurality of image frames generated based on the X-ray passed through an object, and an X-ray generator generating the X-ray. The X-ray corresponds to a pulse signal including a plurality of pulses, in which at least one of a pulse rate or a pulse amplitude is variable.

8 Claims, 24 Drawing Sheets

(56) References Cited

U.S. PATENT DOCUMENTS

| | | |
|---|---|---|
| 7,634,308 B2 | 12/2009 | Ogawa |
| 7,983,391 B2 | 7/2011 | Machan et al. |
| 8,260,025 B2 | 9/2012 | Walimbe et al. |
| 8,340,744 B2 | 12/2012 | Bredno et al. |
| 9,031,186 B2 | 5/2015 | Nambu |
| 2002/0150211 A1 | 10/2002 | Schmitz et al. |
| 2004/0127789 A1 | 7/2004 | Ogawa |
| 2006/0215815 A1 | 9/2006 | Rasche |
| 2008/0107233 A1* | 5/2008 | Sakaguchi ........... A61B 6/4233 378/91 |
| 2008/0319309 A1 | 12/2008 | Bredno et al. |
| 2010/0272238 A1 | 10/2010 | Machan et al. |
| 2011/0235889 A1 | 9/2011 | Spahn |
| 2012/0163534 A1 | 6/2012 | Nambu |
| 2012/0215095 A1 | 8/2012 | Av-Shalom et al. |
| 2013/0216025 A1 | 6/2013 | Chan et al. |
| 2014/0051991 A1 | 2/2014 | Sakaguchi et al. |
| 2014/0341350 A1 | 11/2014 | Muroi et al. |
| 2018/0317865 A1 | 11/2018 | Sakaguchi et al. |

FOREIGN PATENT DOCUMENTS

| | | |
|---|---|---|
| CN | 101721220 | 6/2010 |
| CN | 101803931 | 8/2010 |
| CN | 102469972 | 5/2012 |
| CN | 103179916 | 6/2013 |
| JP | 2000-279400 | 10/2000 |
| JP | 2003-209747 | 7/2003 |
| JP | 2005-270656 | 10/2005 |
| JP | 2008-136800 | 6/2008 |
| JP | 2013-176551 | 9/2013 |

OTHER PUBLICATIONS

International Search Report dated Jan. 22, 2016 issued in corresponding International Patent Application PCT/KR2015/010847.
Extended European Search Report dated Apr. 25, 2018 in corresponding European Patent Application No. 15850258.3, pp. 16.
Chinese Office Action dated Sep. 3, 2019 in corresponding Chinese Patent Application No. 201580055970.4.
European Office Action dated Jun. 25, 2019 in corresponding European Patent Application No. 15850258.3.

* cited by examiner

X-RAY APPARATUS AND X-RAY IMAGING METHOD

RELATED APPLICATIONS

This application claims the benefits of Korean Patent Application No. 10-2014-0158911, filed on Nov. 14, 2014, in the Korean Intellectual Property Office, and Provisional U.S. Patent Application No. 62/064,707, filed on Oct. 16, 2014, in the U.S. PTO, the disclosures of which are incorporated herein in their entirety by reference.

BACKGROUND

1. Field

One or more exemplary embodiments relate to an X-ray apparatus and an X-ray imaging method, and more particularly, to an X-ray imaging apparatus and method which may acquire a plurality of image frames by radiating a pulse type X-ray toward an object.

2. Description of the Related Art

An X-ray apparatus is a medical imaging apparatus that acquires images of internal structures of an object by transmitting an X-ray which passes through the human body. The X-ray apparatus may acquire medical images of an object in a shorter amount of time compared to other medical imaging apparatuses, such as a magnetic resonance imaging (MRI) apparatus and a computed tomography (CT) apparatus, but the acquired images are not as detailed. Therefore, the X-ray apparatus is widely used in generating simple images of the chest, abdomen, skeleton, nasal sinuses, neck soft tissue, and breast imaging. However, as X-rays are radioactive, X-rays radiated toward the object for X-ray imaging may be harmful to a human body.

As described above, since X-rays are radioactive and are harmful to a human body, an operator needs to minimize the amount of radiation that a patient is exposed to when capturing an image of an object during X-ray imaging.

Also, fluoroscopy imaging is a type of image processing technology for acquiring a continuous X-ray image, much like an X-ray movie, by capturing images of an object in real time for monitoring a medical operation, and flouroscopy may be used for angiography. In detail, an operator may use fluoroscopy in providing X-ray angiography for monitoring a surgical operation.

Since X-ray imaging using fluoroscopy requires a large amount of time, the amount of radiation that a patient is exposed to increases according to an imaging time. Accordingly, the amount of radiation that a patient is exposed to increases based on the number of times that radioactive imaging is performed. Accordingly, for X-ray imaging using fluoroscopy, the amount of radiation that a patient is exposed to needs to be reduced.

Alternatively, in order to provide an accurate diagnosis of a patient, a high quality X-ray image acquired by reducing various errors existing in the image is necessary. For example, for a moving object, a motion artifact may be generated in an X-ray image. Accordingly, an apparatus and method of preventing image degradation due to motion by reducing a motion artifact is provided. In order to increase accuracy of an image, an X-ray of over a predetermine value is radiated toward the object to perform X-ray imaging. Since the amplitude of a signal obtained to capture an X-ray image is proportional to the dose of radiated X-ray toward the object, when the dose of radiated X-ray is reduced, image quality of a captured image of an object may be decreased.

Thus, in performing X-ray imaging or fluoroscopy imaging, an X-ray apparatus and method which are able to acquire a high quality X-ray image while reducing the amount of radiation that the object is exposed to is needed.

SUMMARY

One or more embodiments include X-ray apparatus and an X-ray imaging method which may reduce an amount of radiation to which an object is exposed.

One or more embodiments include an X-ray apparatus and an X-ray imaging method which may reduce a the amount of radiation that an object is exposed to in fluoroscopy X-ray imaging One or more embodiments include an X-ray apparatus and an X-ray imaging method which may acquire a fluoroscopy image having an improved image quality.

Additional aspects will be set forth in part in the description which follows and, in part, will be apparent from the description, or may be learned by practice of the presented embodiments.

According to one or more embodiments of an X-ray apparatus includes a controller controlling generation of an X-ray and adjusting at least one of a plurality of image frames generated based on the X-ray passed through an object, and an X-ray generator generating the X-ray, in which the X-ray corresponds to a pulse signal including a plurality of pulses, in which at least one of a pulse rate or a pulse amplitude is variable.

The controller may adjust at least one of the pulse rate and the pulse amplitude of the pulse signal based on a movement of the object or body.

The controller may adjust at least one of the pulse rate and the pulse amplitude of the pulse signal based on a target object located in the object.

The controller may adjust at least one of the pulse rate and the pulse amplitude of the pulse signal based on a movement speed of the target object.

The controller may adjust at least one of the plurality of image frames based on at least one of the plurality of image frames corresponding to at least one of the plurality of pulses.

The pulse signal may include a first section including at least one of the plurality of pulses and a second section including at least one of the plurality of pulses, and the controller may adjust at least one of the plurality of image frames corresponding to the at least one of the plurality of pulses included in the second section based on an image frame which is among the plurality of image frames and corresponds to at least one reference pulse among the plurality of pulses included in the first section.

The respective pulse rates of the plurality of pulses included in the second section may be equal to or less than a pulse rate of at least one of the plurality of pulses included in the first section, and the respective pulse amplitudes of the plurality of pulses included in the second section may be equal to or less than a pulse amplitude of at least one of the plurality of pulses included in the first section.

The first section of the pulse signal may include at least one of the plurality of pulses that are applied while the target object moves through a first portion of the object, the second section of the pulse signal may include at least one of the plurality of pulses that are applied while the target object moves through a second portion of the object, and the target object may move slower in through the second portion than in the first portion.

The first portion may be a region of the object including a first blood vessel, and the second portion may be a region of the object including a second blood vessel which is thinner than the first blood vessel.

The controller may acquire shape information indicating a shape of the object at at least one time point and adjust at least one of the plurality of image frames based on the shape information.

The shape information may include information indicating an anatomical structure of the object.

The shape information may include at least one of a feature map indicating a shape of the object and an edge map indicating a surface of the object.

The controller may generate at least one interpolated image frame located between the plurality of image frames based on at least one of the plurality of image frames.

The controller may control the variation of the pulse amplitude of the pulse signal.

The pulse signal may include a reference pulse and a first pulse adjacent to the reference pulse and having an amplitude smaller than an amplitude of the reference pulse, and the controller may generate an adjusted first image frame by adjusting a first image frame corresponding to the first pulse based on a reference image frame corresponding to the reference pulse.

The controller may adjust a movement of the object included in the first image frame based on shape information of the object acquired based on the reference image frame.

The pulse signal may include a second pulse adjacent to the first pulse and having an amplitude smaller than the amplitude of the first pulse, and the controller may generate an adjusted second image frame by adjusting a second image frame corresponding to the second pulse based on the adjusted first image frame The controller may control the variation of the pulse rate of the pulse signal.

The pulse signal may include a first section including the at least one of the plurality of pulses and having a first pulse rate and a second section including at least one of the plurality of pulses and having a second pulse rate lower than the first pulse rate.

The controller may generate, based on a reference image frame which corresponds to a reference pulse output at a first time point included in the first section and a first image frame which corresponds to a first pulse output at a second time point adjacent to the first time point, an interpolated image frame corresponding to a third time point between the first time point and the second time point.

The controller may acquire information about a movement of the object and generate the interpolated image frame based on acquired information.

The controller may control the variation of the pulse rate and the pulse amplitude of the pulse signal.

The pulse signal may include a first section including at least one reference pulse and a second section including at least one first pulse having a pulse rate and pulse amplitude lower than the pulse rate and the pulse amplitude in the first section.

The controller may adjust at least one first image frame corresponding to the at least one first pulse based on a reference image frame corresponding to the reference pulse, and generate an interpolated image frame arranged between the reference image frame and the at least one first image frame based on the reference image frame and the at least one first image frame.

The controller may adjust at least one of the plurality of image frames representing a field of view (FOV).

The controller may adjust at least one of the plurality of image frames representing a non-region of interest (non-ROI).

The controller may adjust at least one of the plurality of image frames representing a region of interest (ROI).

The controller may generate a fluoroscopy X-ray image based on the at least one adjusted image frame.

The controller may generate a fluoroscopy X-ray image based on the at least one interpolated image frame and the at least one adjusted image frame.

The X-ray apparatus may further include a display displaying the fluoroscopy X-ray image.

According to one or more embodiments of an X-ray apparatus includes an X-ray generator generating an X-ray that corresponds to a pulse signal including a plurality of pulses and having a pulse rate that is variable and radiating the generated X-ray toward an object, and a controller acquiring a plurality of final image frames that have a frame rate higher than the pulse rate of the pulse signal based on a plurality of image frames generated based on the X-ray.

The controller may acquire information about a movement of the object and generate at least one interpolated image frame based on the acquired information and at least one of the plurality of image frames.

The plurality of final image frames may include the plurality of image frames and the at least one interpolated image frame.

The controller may adjust the pulse rate of the pulse signal based on a movement of a target object included in the object.

According to one or more embodiments of an X-ray apparatus includes an X-ray generator generating an X-ray that corresponds to a pulse signal including a plurality of pulses and having a pulse amplitude that is variable and radiating the generated X-ray toward an object, and a controller adjusting at least one of a plurality of image frames generated by using the X-ray based on at least one reference image frame included in the plurality of image frames imaged according to the X-ray.

The controller may acquire shape information based on the at least one reference image frame and may adjust at least one of the plurality of image frames based on the shape information, wherein the shape information indicates a shape of the object at at least one of time points.

The controller may adjust the pulse amplitude of the pulse signal based on a movement of a target object included in the object.

According to one or more embodiments of an X-ray apparatus includes an X-ray generator generating an X-ray that corresponds to a pulse signal including a plurality of pulses and having a pulse rate and an amplitude that are variable and radiating the generated X-ray toward an object, and a controller acquiring a plurality of final image frames that have a frame rate higher than the pulse rate of the pulse signal based on at least one reference image frame of a plurality of image frames generated based on the X-ray.

The controller may generate at least one interpolated image frame based on information about a movement of the object.

The controller may generate at least one adjusted image frame by adjusting at least one of the plurality of image frames based on the at least one reference image frame.

The controller may adjust the pulse rate and the pulse amplitude of the pulse signal based on a movement of a target object included in the object.

According to one or more embodiments of an X-ray apparatus includes a controller controlling generation of a pulse signal and generation of an X-ray corresponding to the pulse signal, and an X-ray generator generating the X-ray, wherein the pulse signal includes a plurality of pulses included in one cycle having a predetermined pattern, and at least two of the pulses are different from each other.

At least two of the plurality of pulses included in the cycle may have a pulse rate and pulse amplitude, at least one of the pulse rate and the pulse amplitude being different from each other.

The predetermined pattern may be set based on a movement of the object.

The predetermined pattern may be set based on a movement of a target object included in the object.

According to one or more embodiments of an X-ray imaging method includes generating an X-ray, acquiring a plurality of image frames generated based on the X-ray passed through an object, and adjusting at least one of the plurality of image frames, wherein the X-ray corresponds to a pulse signal including a plurality of pulses and having at least one of a pulse rate or a pulse amplitude that are variable.

The generating of the X-ray may include adjusting at least one of the pulse rate and the pulse amplitude of the pulse signal based on a movement of the object.

The generating of the X-ray may include adjusting at least one of the pulse rate and the pulse amplitude of the pulse signal based on a movement of a target object included in the object.

The generating of the X-ray may include adjusting at least one of the pulse rate and the pulse amplitude of the pulse signal based on a movement speed of the target object.

The adjusting of at least one of the plurality of image frames may include adjusting at least one of the plurality of image frames based on at least one of the plurality of image frames corresponding to at least one of the plurality of pulses.

The pulse signal may include a first section including at least one of the plurality of pulses and a second section including at least one of the plurality of pulses, and the adjusting of at least one of the plurality of image frames may include adjusting at least one of the plurality of image frames corresponding to at least one of the plurality of pulses included in the second section based on an image frame which is among the plurality of image frames and corresponds to at least one reference pulse among the plurality of pulses included in the first section.

At least one of pulse rate and pulse amplitude of at least one of the plurality of pulses included in the second section may respectively have a value equal to or less than at least one pulse rate and pulse amplitude of at least one of the plurality of pulses included in the first section.

The first section may include at least one of the plurality of pulses applied during which the target object moves through a first portion of the object, and the second section may include at least one of the plurality of pulses applied during which the target object moves through a second portion of the object where the target object moves slower than in the first portion, wherein the first portion is a region of the object including a first blood vessel and the second portion is a region of the object including a second blood vessel which is thinner than the first blood vessel.

The adjusting of at least one of the plurality of image frames may include acquiring shape information indicating the object at at least one of time points and adjusting at least one of the plurality of image frames based on the shape information.

The shape information may include at least one of a feature map indicating a shape of the object and an edge map indicating a surface forming the object.

The method may further include generating at least one interpolated image frame located between the plurality of image frames based on at least one of the plurality of image frames.

The method may further include generating a fluoroscopy X-ray image based on the at least one adjusted image frame.

The method may further include generating a fluoroscopy X-ray image based on the at least one interpolated image frame and the at least one adjusted image frame.

The method may further include displaying the fluoroscopy X-ray image.

According to one or more embodiments of an X-ray imaging method includes generating an X-ray that corresponds to a pulse signal including a plurality of pulses and having a pulse rate that is variable and radiating the X-ray toward an object, acquiring a plurality of image frames based on the generated X-ray radiated toward the object, and acquiring a plurality of final image frames based on the plurality of image frames, wherein the plurality of final image frames have a frame rate higher than a pulse rate of the pulse signal.

The acquiring of the plurality of final image frames may include acquiring information about a movement of the object and generating at least one interpolated image frame based on the acquired information and at least one of the plurality of image frames, and wherein the plurality of final image frames include the at least one interpolated image frame.

According to one or more embodiments of an X-ray imaging method includes generating an X-ray corresponds to a pulse signal including a plurality of pulses and having a pulse amplitude that is variable and radiating the X-ray toward an object, acquiring a plurality of image frames based on the radiated X-ray and the object, and adjusting at least one of the plurality of image frames based on at least one reference image frame of the plurality of image frames.

The adjusting of the at least one of the plurality of image frames may include acquiring shape information based on the at least one reference image frame, and adjusting at least one of the plurality of image frames based on the shape information wherein the shape information indicates a shape of the object at at least one of time points.

According to one or more embodiments of an X-ray imaging method includes generating an X-ray that corresponds to a pulse signal including a plurality of pulses and having a pulse rate and an amplitude that are variable and radiating the generated X-ray toward an object, acquiring a plurality of image frames based on the generated X-ray radiated toward the object, and acquiring a plurality of final image frames that have a frame rate higher than the pulse rate of the pulse signal based on at least one reference image frame of the plurality of image frames generated based on the X-ray.

The acquiring of the plurality of final image frames may include generating at least one interpolated image frame based on information about a movement of the object, and acquiring the plurality of final image frames including the at least one interpolated image frame.

The acquiring of the plurality of final image frames may include generating at least one interpolated image frame by adjusting at least one of the plurality of image frames based on the at least one reference image frame, and acquiring the plurality of final image frames including the at least one interpolated image frame.

According to one or more embodiments of an X-ray imaging method includes generating a pulse signal, and generating an X-ray corresponding to the pulse signal, wherein the pulse signal may include a plurality of pulses included in one cycle having a predetermined pattern, and at least two of the pulses are different from each other.

At least two of the plurality of pulses included in the cycle may have a pulse rate and pulse amplitude, at least one of the pulse rate and the pulse amplitude being different from each other.

One or more embodiments include a non-transitory computer readable storage storing an X-ray imaging method, the method including generating an X-ray, acquiring a plurality of image frames generated based on the X-ray passed through an X-ray object, and adjusting at least one of the plurality of image frames, where the X-ray corresponds to a pulse signal including a plurality of pulses and having at least one of a pulse rate or a pulse amplitude that are variable.

One or more embodiments include a real time X-ray method, the method including generating a X-rays where the X-rays have pulses and allowing one or both of pulse rate and pulse amplitude to be varied responsive to tracking target object motion within a body being X-rayed, acquiring image frames of the body through which the X-ray has passed and displaying image frames from among captured image frames, artifact corrected image frames and interpolated virtual image frames. The pulse rate may increase as motion speed increases and the pulse rate may decrease as motion speed decreases. The pulse amplitude may increase as motion speed increases and the pulse amplitude may decrease as motion speed decreases.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
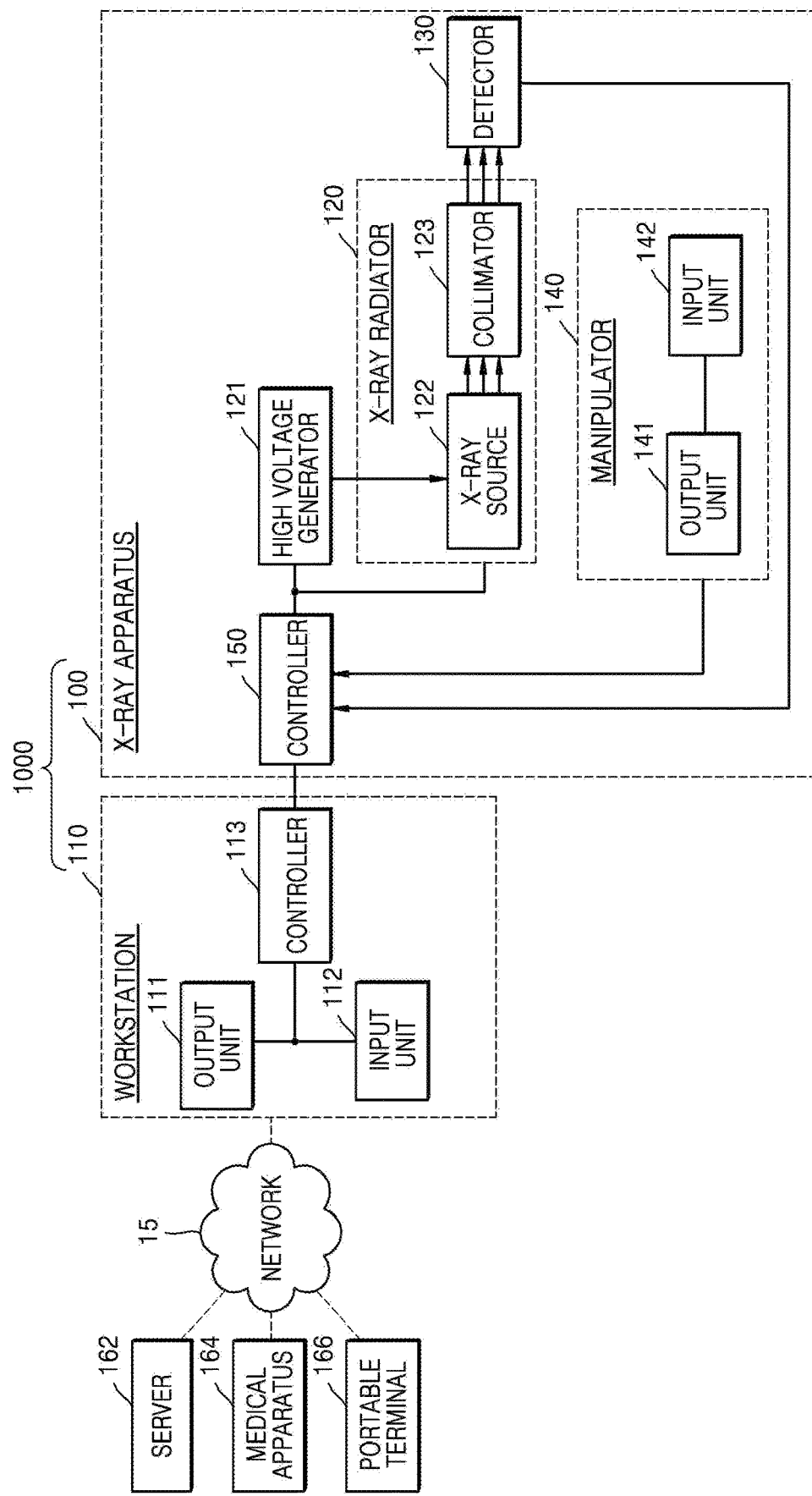
FIG. 1 is a block diagram of an X-ray system.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Advantages and features of one or more embodiments accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and in this case, the meaning of the selected terms will be described in detail in the detailed description. Thus, the terms used herein may be defined based on the meaning of the terms together with the description throughout the specification.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.]

In addition, an "object" may be a human, an animal, or a part of a human or animal. For example, the object may be an organ (e.g., the liver, heart, womb, brain, breast, or abdomen), a blood vessel, or a combination thereof. The object may be a phantom. The term phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest imaging, simple abdomen imaging, simple skeleton imaging, simple nasal sinuses imaging, simple neck soft tissue imaging, and breast imaging.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube is set in a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of thermal electrons increases, and accordingly, energy of the X-ray (energy of a photon) that is generated when thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray amount (the number of X-ray photons) generated when thermal electrons collide with the target material is increased.

Therefore, the energy of the X-ray may be adjusted according to the tube voltage, and the intensity of the X-ray or the X-ray amount may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray imaging. The controller 150 may control or manipulate the X-ray apparatus 100 according to the information received by the input unit 142. The output unit 141 may output sound representing information related to an imaging operation, such as the X-ray radiation, under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. In some embodiments, the controllers 113 and 150 may be integrated into a single controller, and the single controller may be included in only one of the workstation 110 and the X-ray apparatus 100.

Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed in two steps.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141, so that the output units 111 and 141 output a predetermined sound, and the object may receive the radiation of the X-ray. The output units 111 and 141 may also output a sound representing information related to imaging in addition to the X-ray radiation. In FIG. 1, the output unit 141 is included in the manipulator 140; however, the embodiments are not limited thereto, and the output unit 141 or a portion of the output unit 141 may be located elsewhere. For example, the output unit 141 may be located on a wall of an examination room in which the X-ray imaging of the object is performed.

The controllers 113 and 150 control locations of the X-ray radiator 120 and the detector 130, imaging timing, and imaging conditions, according to imaging conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the control units 113 and 150 adjust the location of the detector 130 according to a predetermined imaging condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator (not shown) may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166, such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

As in the X-ray system 1000 described with reference to FIG. 1, the X-ray apparatus according to an exemplary embodiment may be all electronic apparatuses that are capable of performing and/or controlling X-ray imaging. In detail, the X-ray apparatus according to an exemplary embodiment may be all electronic apparatuses that are capable of performing and/or controlling X-ray imaging by radiating a pulse type X-ray.

In detail, a C-arm X-ray apparatus that may acquire a plurality of X-ray images during consecutive time sections may be used as the X-ray apparatus according to an exemplary embodiment. Also, the C-arm X-ray apparatus may include an interventional X-ray apparatus, an interventional angiographic C-arm X-ray apparatus, or a surgical C-arm X-ray apparatus.

Also, the X-ray apparatus according to an exemplary embodiment may be applicable to all X-ray apparatuses which may acquire an X-ray motion picture by performing X-ray imaging for consecutive predetermined time sections. In detail, the X-ray apparatus according to an exemplary embodiment may be applicable to all X-ray apparatuses that may perform X-ray imaging while tracking a moving object or target object, by freely controlling the position of an X-ray source.

The C-arm X-ray apparatus is described below in detail with reference to FIG. 2 and FIGS. 3A to 3C.

Figure 2:
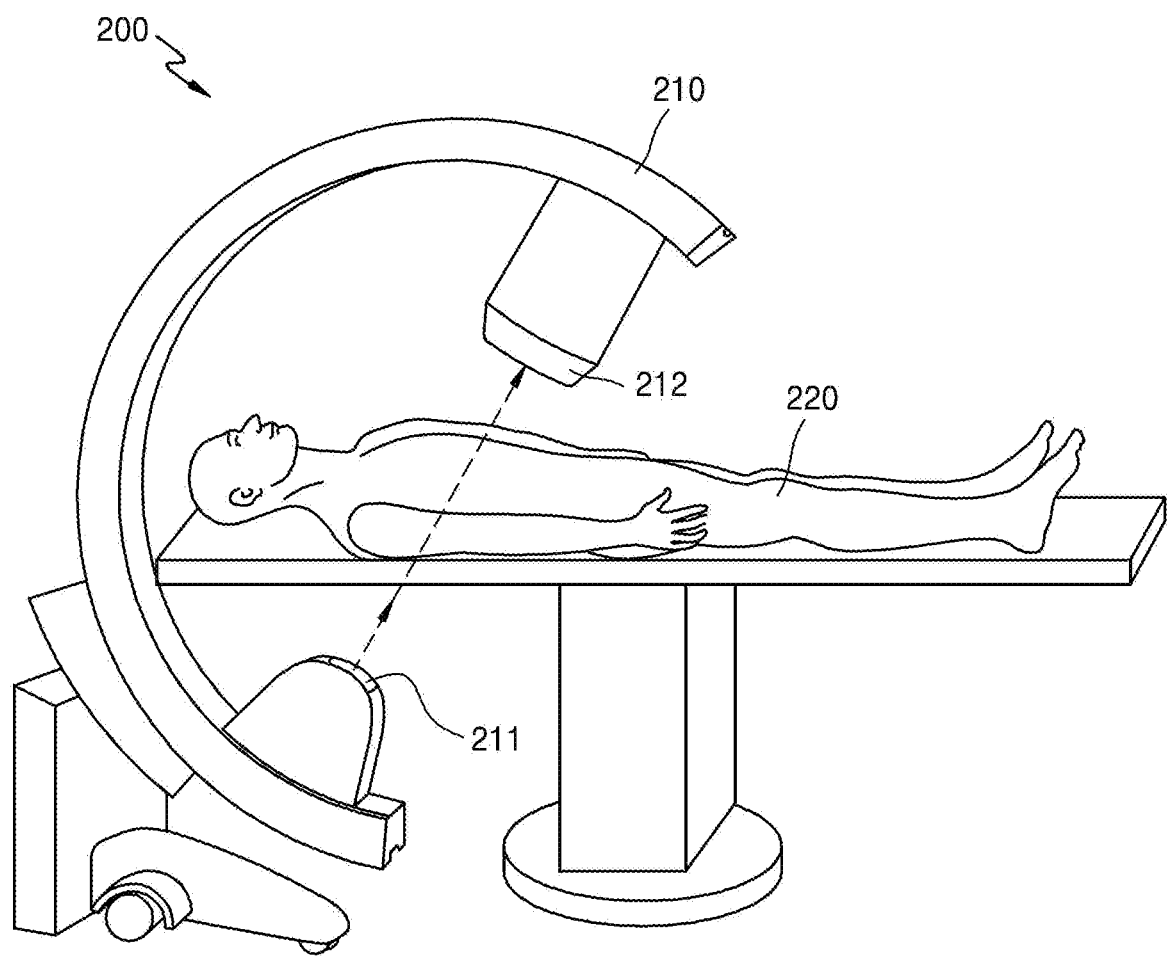
FIG. 2 illustrates a C-arm X-ray apparatus to which an exemplary embodiment may be applicable.

FIG. 2 illustrates a C-arm X-ray apparatus 200 to which an exemplary embodiment may be applicable.

Referring to FIG. 2, the C-arm X-ray apparatus 200 has a C-arm 210 having a "C" shape and may perform X-ray imaging continuously for a predetermined time. An X-ray radiator 211 is provided at one end of the C-arm 210, and a detector 212 is provided at the other end of the C-arm 210. Since the X-ray radiator 211 and the detector 212 identically correspond to the X-ray radiator 120 and the detector 130 of FIG. 1, respectively, redundant descriptions thereof are omitted.

The user may image an object 220 at various positions or angles through the C-arm 210. For example, the user may acquire a fluoroscopic image by imaging a region of interest (ROI) of the object 220 while rotating the C-arm 210 or moving the C-arm 210 vertically or horizontally. Accordingly, compared to a general fixed-type X-ray apparatus, the user may efficiently photograph the object during a continuous time period by using the C-arm X-ray apparatus 200. Since the structure of the C-arm X-ray apparatus 200 is obvious to one of ordinary skill in the art, detailed descriptions thereof are omitted.

The C-arm X-ray apparatus 200 may be useful for acquiring a plurality of X-ray images during a continuous time period, or acquiring an X-ray motion picture. For example, the C-arm X-ray apparatus 200 may be useful for medical operations, such as X-ray angiography or a surgical operation. When a medical doctor needs to precisely examine a patient for diagnosis of a patient having a blood vessel disease, the medical doctor performs X-ray imaging continuously during examination. A state of a blood vessel of a patient is examined through a fluoroscopic image that is an X-ray motion picture acquired in real time. Accordingly, in a medical operation such as X-ray angiography, the fluoroscopic image is acquired by continuously radiating an X-ray toward the object during the operation.

For example, for angiography, X-ray imaging may be performed by arranging a guide wire around the object to be examined, or by injecting a drug solution using a thin needle or a catheter.

In another example, for a surgical operation, in performing an operation by injecting a catheter, a stent, or a syringe needle into a human body, an operator such as a medical doctor checks whether the catheter, for example, may be correctly inserted into a target position of an object. Accordingly, the user may perform an operation by acquiring a fluoroscopic image during the operation and checking the position of a target object such as a catheter through the acquired fluoroscopic image. In the following description, an X-ray motion picture acquired according to the fluoroscopy imaging may be referred to as the fluoroscopic image.

Also, when a plurality of image frames are acquired by radiating a pulse type X-ray corresponding to the pulse signal toward the object, the fluoroscopic image may be acquired by arranging the image frames in order of time and reproducing the image frames.

The present exemplary embodiment may be useful for a case in which a guide wire, a syringe needle, a catheter, or a stent is arranged or inserted in the object, and X-ray imaging is performed on the object by using the C-arm X-ray apparatus 200. In detail, the present exemplary embodiment may be useful for a case in which a plurality of X-ray images or an X-ray motion picture is needed in order to continuously check a motion of the above-described guide wire, syringe needle, catheter, or stent during a examination time period.

In the following description, a material that is inserted into the object to be observed by an operator is referred to as the target object. In detail, a material other than human tissues, such as a guide wire, a syringe needle, a catheter, or a stent, which is inserted into the human body, may be referred to as the target object.

Figure 3A:
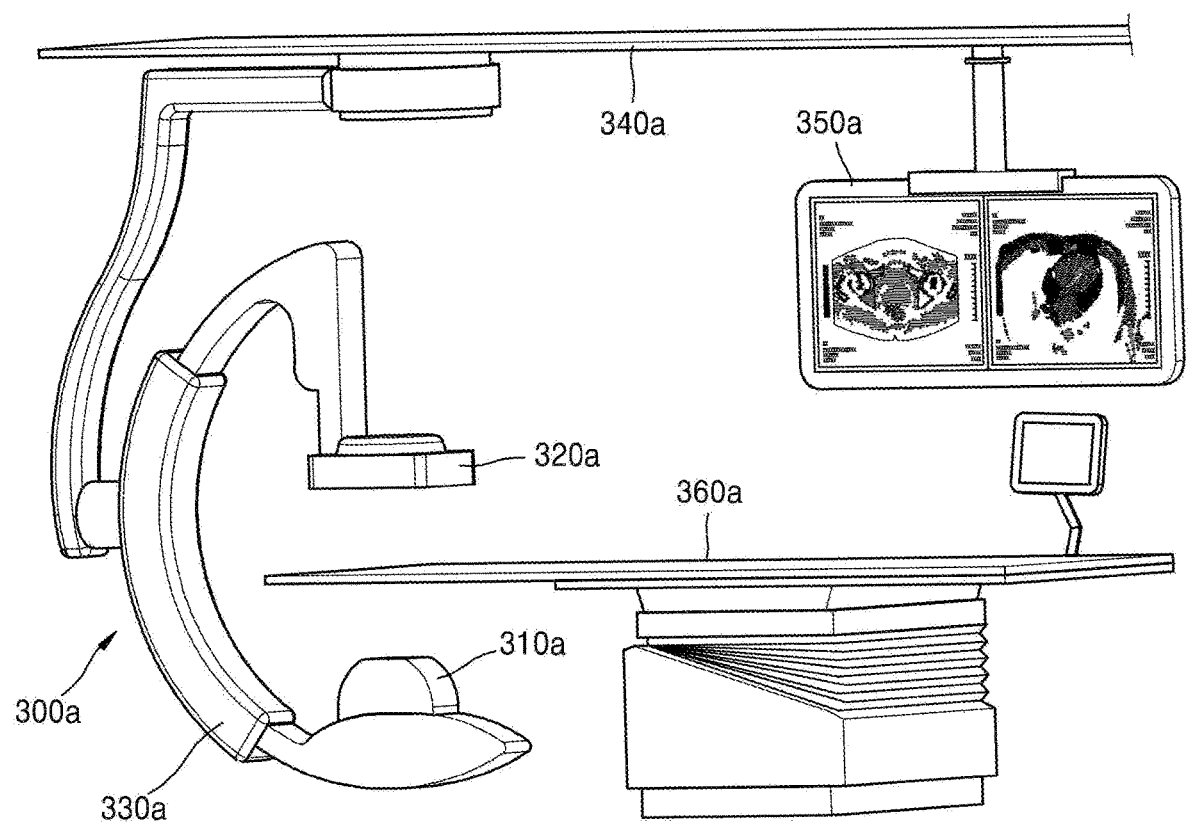
FIGS. 3A, 3B, and 3C illustrate various shapes of the C-arm X-ray apparatus.
Figure 3B:
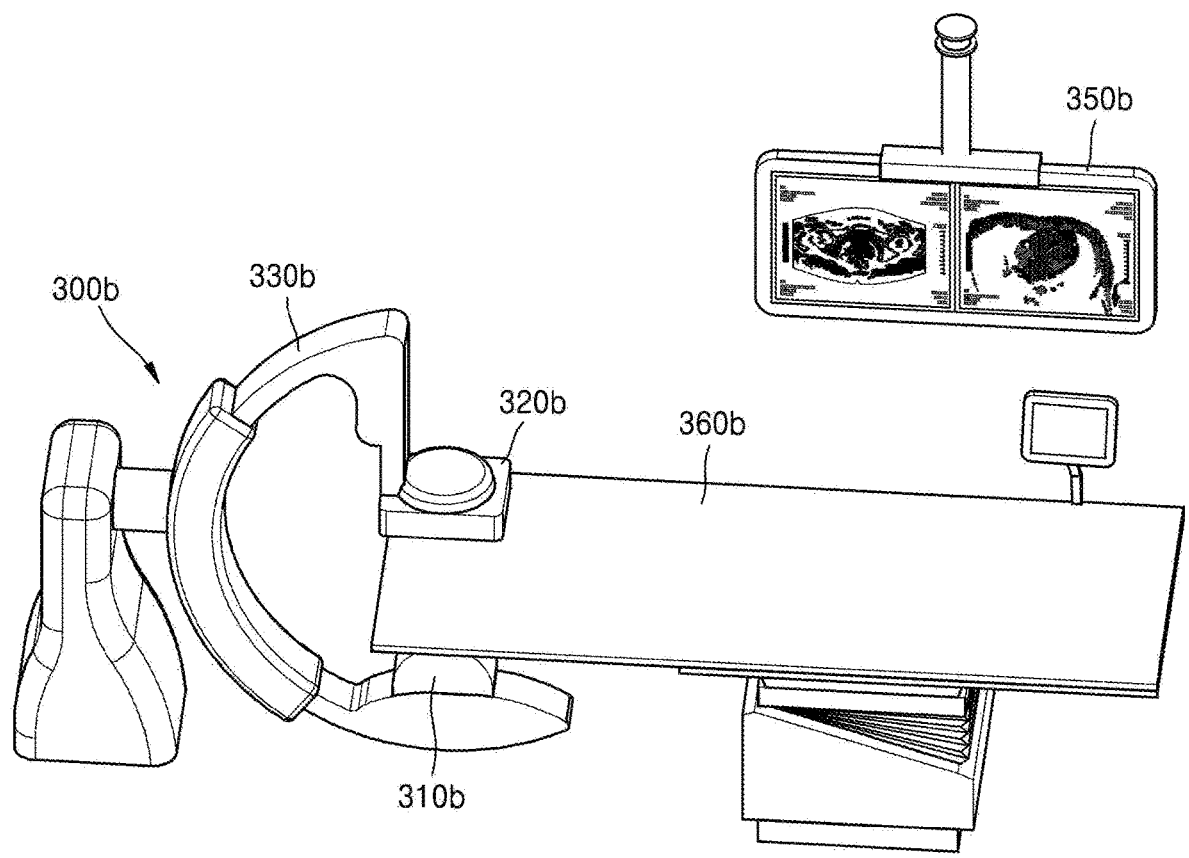
Figure 3C:
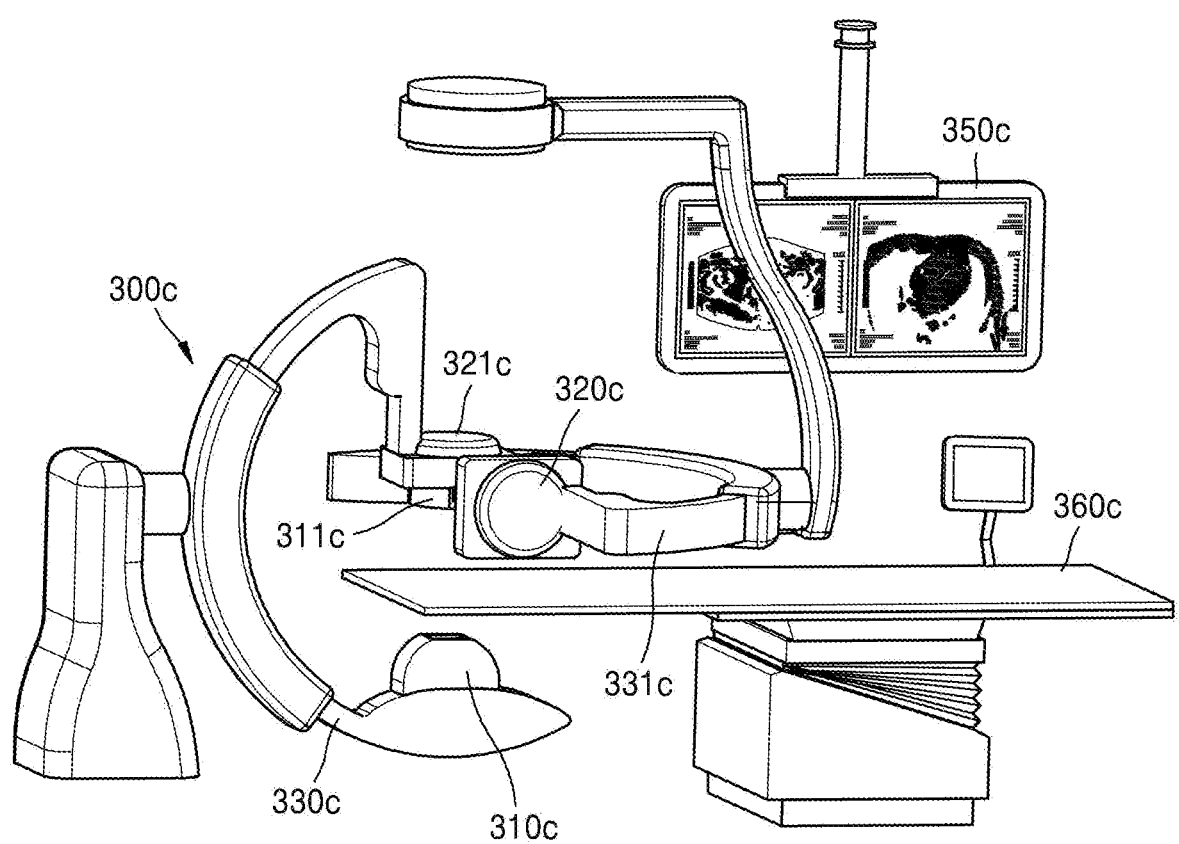

FIGS. 3A, 3B, and 3C illustrate various shapes of the C-arm X-ray apparatus 200.

In detail, FIG. 3A illustrates a ceiling-mounted C-arm X-ray apparatus 300a. FIG. 3B illustrates a floor-mounted C-arm X-ray apparatus 300b. FIG. 3C illustrates a ceiling/floor-mounted C-arm X-ray apparatus 300c. The ceiling/floor-mounted C-arm X-ray apparatus 300c of FIG. 3C may obtain information for the same time period at twice the amount of information compared to the cell-mounted C-arm X-ray apparatus 300a or the floor-mounted C-arm X-ray apparatus 300b.

In general, the C-arm X-ray apparatuses 300a, 300b, and 300c may include X-ray sources 310a, 310b, 310c, and 311c, detectors 320a, 320b, 320c, and 321c, C-arms 330a, 330b, 330c, and 331c connecting the X-ray sources 310a, 310b, 310c, and 311c and detectors 320a, 320b, 320c, and 321c and controlling the positions of the X-ray sources 310a, 310b, 310c, and 311c and detectors 320a, 320b, 320c, and 321c, displays 350a, 350b, and 350c, and tables 360a, 360b, and 360c where the object is placed.

The C-arm X-ray apparatuses 300a, 300b, and 300c of FIGS. 3A, 3B, and 3C may be included in the X-ray apparatus 100 of FIG. 1 or identically corresponding thereto. In detail, the X-ray sources 310a, 310b, 310c, and 311c, the detectors 330a, 320b, 320c, and 321c, and the displays 350a, 350b, and 350c of FIGS. 3A, 3B, and 3C may identically correspond to the X-ray source 122, the detector 130, and the output units 111 and 141 of FIG. 1. Accordingly, redundant descriptions thereof are omitted.

Also, the ceiling-mounted C-arm X-ray apparatus 300a of FIG. 3A may further include a guide rail 340a for moving the positions of the X-ray sources 310a, 310b, 310c, and 311c, the detectors 320a, 320b, 320c, and 321c, and the C-arms 330a, 330b, 330c, and 331c.

The guide rail 340a is arranged on a ceiling of an examination room where the C-arm X-ray apparatus 300a or 300c is arranged. A roller (not shown) capable of moving along the guide rail 340a is arranged on the guide rail 340a and thus the positions of the X-ray source 310a, the detector 320a, and the C-arm 330a may be moved. In detail, the C-arm X-ray apparatus 300a may perform a longitudinal motion and a lateral motion through the guide rail 340a. The longitudinal motion is to move the position of the X-ray source 310a in a vertical axis direction. For example, when a user who currently captures an image of a left portion of the chest of a patient tries to capture an image of a right portion of the chest, the user may adjust the position of the X-ray source 310a through the longitudinal motion of the C-arm 330a. The lateral motion of the C-arm 330a is to move the position of the X-ray source 310a in a horizontal axis direction. For example, when a user who currently captures an image of the abdomen of a patient tries to capture an image of the chest of the patient, the user may adjust the position of the X-ray source 310a through the longitudinal motion of the C-arm 330a.

The above-described guide rail 340a may also be arranged in the C-arm X-ray apparatus 300c of FIG. 3C.

The user may image the object at various positions or angles by using the C-arms 330a, 330b, 330c, and 331c and/or the tables 360a, 360b, and 360c. For example, the user may acquire a fluoroscopic image by imaging an ROI of the object while rotating or vertically or horizontally moving the C-arms 330a, 330b, 330c, and 331c and/or the tables 360a, 360b, and 360c. Accordingly, the user may efficiently image a moving object by using the C-arm X-ray apparatuses 300a, 300b, and 300c, compared to the general fixed-type X-ray apparatus.

Accordingly, the C-arm X-ray apparatuses 300a, 300b, and 300c may effectively capture an image of a moving object or a moving target object. In detail, the C-arm X-ray apparatuses 300a, 300b, and 300c may perform image capturing while moving the C-arms 330a, 330b, 330c, and 331c to track a moving object or a moving target object, an X-ray image focusing on the object and the target object may be acquired.

Thus, the X-ray apparatus according to an exemplary embodiment is applicable to the C-arm X-ray apparatuses 300a, 300b, and 300c respectively described with reference to FIGS. 3A, 3B, and 3C, and thus a fluoroscopic image may be acquired by performing X-ray imaging on a moving object or a moving target object.

Figure 4A:
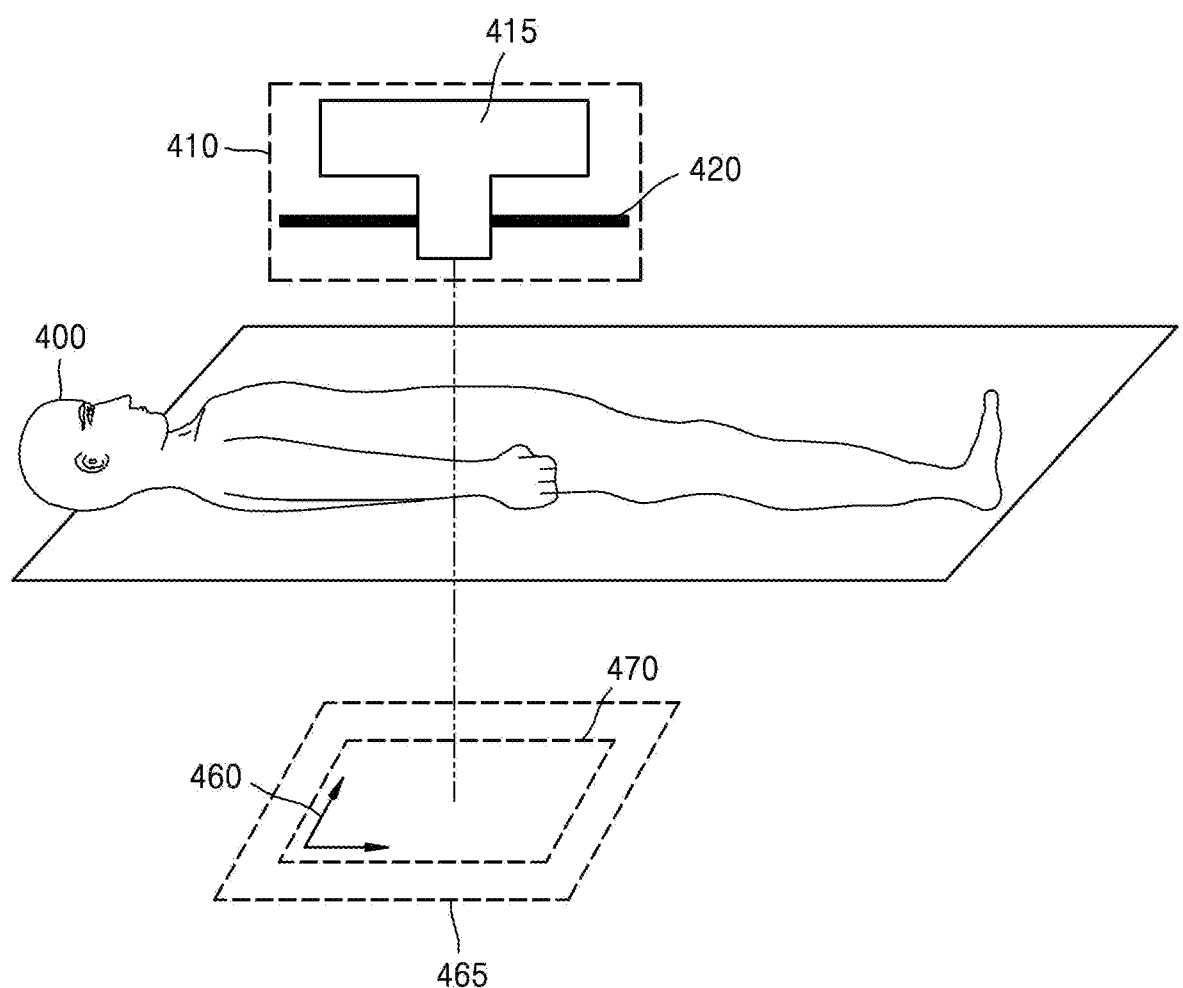
FIG. 4A is a view for describing acquisition of an image frame.

FIG. 4A is a view for describing acquisition of an image frame.

Referring to FIG. 4A, the X-ray apparatus includes an X-ray radiator 410 and a detector 465. Since the X-ray radiator 410 and the detector 465 identically correspond to the X-ray radiator 120 and the detector 130 of FIG. 1, redundant descriptions thereof are omitted.

Referring to FIG. 4A, the X-ray apparatus performs X-ray imaging on the abdomen of a patient 400 as an object. The X-ray radiator 410 includes an X-ray source 415 and a collimator 420.

The X-ray radiator 410 radiates an X-ray generated from the X-ray source 415 toward an object that is the abdomen of the patient 400.

The detector 465 detects the X-ray that passes through the object. The X-ray detected by the detector 465 is used for imaging of an object region 460 through which the X-ray passes.

Also, the X-ray radiated from the X-ray source 415 may be a pulse type X-ray having a pulse form. The pulse type X-ray is described below in detail with reference to FIG. 5.

In the following description, an example in which the X-ray used for X-ray imaging is a pulse type X-ray that is radiated in the form of a pulse is illustrated and described.

Figure 4B:
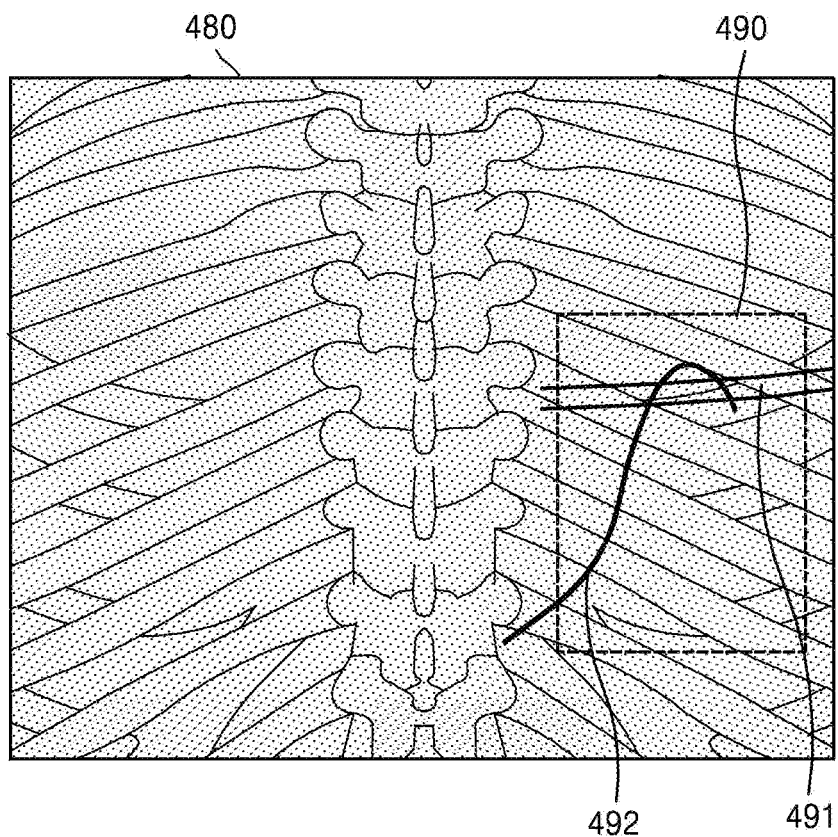
FIG. 4B is a view for describing an acquired image frame.

FIG. 4B is a view for describing an acquired image frame.

Referring to FIG. 4B, the X-ray apparatus may acquire an X-ray image 480 by imaging the object region 460 through which the X-ray radiated from the X-ray source 415 passes, based on the X-ray detected by the detector 465. In the following description, the X-ray image 480 that is imaged by the X-ray corresponding to one pulse is referred to as the image frame.

The X-ray image 480 is an X-ray image obtained by imaging a blood vessel 491 included in the object and a catheter 492 inserted around the blood vessel 491. Also, an imaged entire region is referred to as a field of view (FOV), and a region set as a major portion of diagnosis of the FOV is referred to as an ROI 490. Also, in the following description, a case in which, when the catheter 492 that is the target object moves, the X-ray apparatus acquires a plurality of the X-ray images 480 during a continuous time period.

Figure 5A:
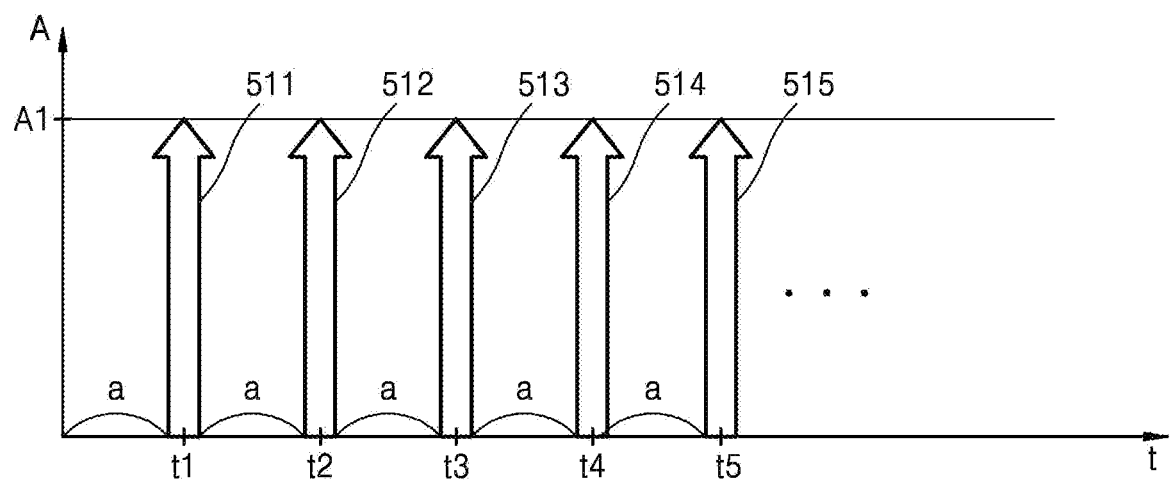
FIGS. 5A and 5B are views for describing a pulse signal used to generate an X-ray.
Figure 5B:
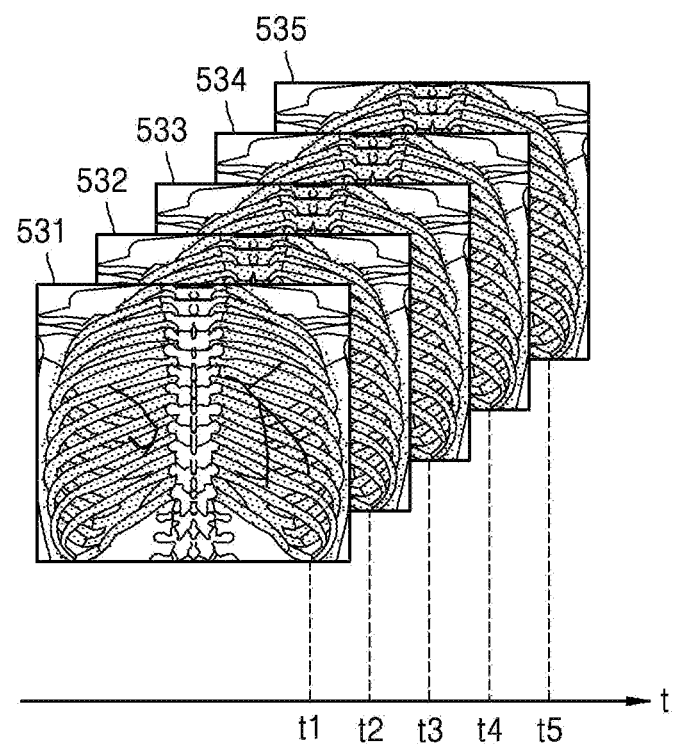

FIGS. 5A and 5B are views for describing a pulse signal used to generate an X-ray.

In detail, FIG. 5A illustrates a pulse signal to generate a pulse type X-ray. In the pulse signal, an x-axis denotes time and y-axis denotes an amplitude A of a pulse signal. FIG. 5B illustrates a plurality of image frames that are imaged when X-ray imaging is performed by using the pulse type X-ray.

Referring to FIG. 1, in order to generate an X-ray, a high voltage generator 121 generates a high voltage to be applied to the X-ray source 122. A high voltage signal generated from the high voltage generator 121 may be a pulse signal having a pulse form. When the high voltage signal generated from the high voltage generator 121 is a pulse signal, an amplification value of the pulse signal indicated on the y-axis may be a voltage unit "kVp". For example, when the pulse signal is a high voltage signal generated from the high voltage generator 121, the pulse amplitude may correspond to a tube voltage applied between the anode and the cathode of an X-ray tube included in the high voltage generator 121. Alternatively, the pulse amplitude may correspond to a tube current flowing between the anode and the cathode of an X-ray tube included in the high voltage generator 121.

A pulse signal may be used as a control signal to generate a high voltage signal in the high voltage generator 121. In this case, the pulse signal is a signal corresponding to the high voltage signal and a y-axis value may be presented as a voltage or current value.

An amount of radiation of the X-ray radiated toward the object is proportional to the pulse amplitude. Accordingly, when the pulse amplitude increases, the amount of radiation may increase and, when pulse amplitude decreases, the amount of radiation may decrease.

Referring to FIG. 5A, the pulse signal may include a plurality of pulses 511, 512, 513, 514, and 515 and may have a predetermined pulse rate. The pulse rate signifies the number of pulses generated for a predetermined time. In detail, the pulse rate signifies the number of pulses output for one second and may be presented in units of pulse per second (pps). To acquire a fluoroscopic image, X-ray imaging may be performed at a pulse rate of, for example, 10 pps, 30 pps, or 60 pps.

The pulse amplitude of a pulse signal is a value corresponding to a high voltage value applied to generate a pulse type X-ray. Also, the amount of the X-ray radiation radiated toward the object is proportional to the pulse amplitude. Accordingly, when the pulse amplitude is large, the amount of the X-ray radiated toward the object is large. When the pulse amplitude is small, the amount of the X-ray radiated is small. Accordingly, the amount of the X-ray radiated toward the object may be reduced by decreasing the pulse amplitude.

One pulse 511, for example, first pulse 511, corresponds to a single shot of X-ray exposure. When a single shot of X-ray exposure corresponding to the first pulse 511 is radiated, a first image 531 which is a frame image may be imaged.

Referring to FIG. 5A, as an example, the amplifications of the pulses 511, 512, 513, 514, and 515 included in the pulse signal are identical to one another. Also, a case in which a pulse rate of a pulse signal is constant is illustrated as an example. Accordingly, referring to FIG. 5A, an interval between one pulse, for example, the pulse 511 and an adjacent pulse, for example, a pulse 512, is constant.

Referring to FIGS. 5A and 5B, when the object is the chest of a patient, the first image 531 that is imaged by the X-ray radiated toward the object corresponding to the first pulse 511 output at a first time point t1. A second image 532 is an image frame that is imaged by the X-ray radiated toward the object corresponding to a second pulse 512 output at a second time point t2. A third image 533 is an image frame that is imaged by the X-ray radiated toward the object corresponding to a third pulse 513 output at a third time point t3. A fourth image 534 is an image frame that is imaged by the X-ray radiated toward the object corresponding to a fourth pulse 514 output at a fourth time point t4. A fifth image 535 is an image frame that is imaged by the X-ray radiated toward the object corresponding to a fifth pulse 515 output at a fifth time point t5. In other words, the image frames 531, 532, 533, 534, and 535 respectively correspond to the pulses 511, 512, 513, 514, and 515.

In the following description, an X-ray apparatus for acquiring and adjusting a plurality of image frames that are imaged by using a pulse type X-ray according to an exemplary embodiment is described below in detail with reference to FIGS. 6 to 15.

The X-ray apparatus according to an exemplary embodiment is applicable to the X-ray system of FIG. 1. Also, the X-ray apparatus according to an exemplary embodiment is applicable to all X-ray systems that radiate pulse type X-rays. Also, the X-ray apparatus according to an exemplary embodiment may be an apparatus for controlling all X-ray systems that radiate the pulse type X-rays. Also, the X-ray apparatus according to an exemplary embodiment may be all image processing apparatus that may process X-ray images acquired by the pulse type X-rays to the object. In detail, the X-ray apparatus according to an exemplary embodiment may be applicable to all medical apparatuses or medical image processing apparatuses that image an X-ray image by using the pulse type X-ray.

Also, the X-ray apparatus according to an exemplary embodiment may be all electronic apparatuses that may acquire an X-ray image by radiating an X-ray which is a pulse-type X-ray generated by using the pulse signal illustrated in FIG. 5A, and process and/or display the acquired X-ray image. For example, the X-ray apparatus according to an exemplary embodiment may be applied to all of an X-ray apparatus radiating a single X-ray, a dual energy X-ray apparatus radiating two X-rays corresponding to two energy bands, and a multi-energy X-ray (MEX) performing X-ray imaging by radiating a plurality of X-rays corresponding to a plurality energy bands.

In detail, the X-ray apparatus according to an exemplary embodiment may be an X-ray apparatus for acquiring a fluoroscopic image which is an X-ray motion picture by radiating the pulse type X-ray toward the object. The fluoroscopy is an image processing technology to acquire an X-ray motion picture by imaging an object in real time for monitoring an operation and may be used for angiography. Also, the X-ray apparatus according to an exemplary embodiment may be an X-ray apparatus for acquiring a digital subtraction angiography (DSA) image. Also, the X-ray apparatus according to an exemplary embodiment may be an X-ray apparatus for acquiring a roadmap image. The roadmap is an X-ray image for checking the position of an operational tool and may be obtained by overlapping a blood vessel image and a fluoroscopic image. The roadmap may be a two-dimensional image or a three-dimensional image.

Figure 6:
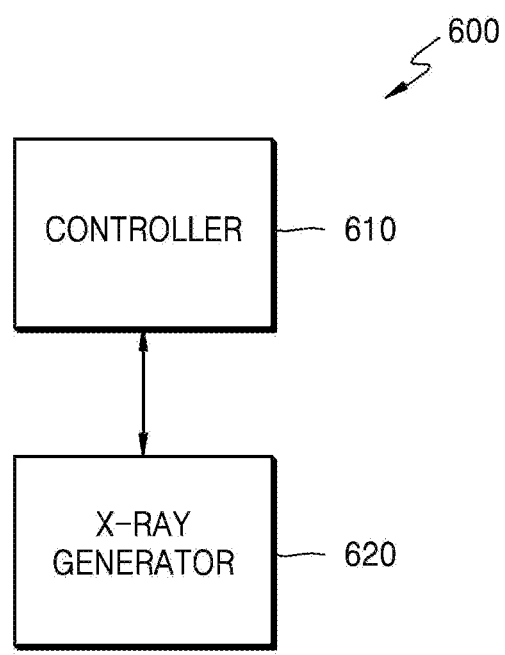
FIG. 6 is a block diagram of an X-ray apparatus according to an exemplary embodiment.

FIG. 6 is a block diagram of an X-ray apparatus 600 according to an exemplary embodiment.

Referring to FIG. 6, the X-ray apparatus 600 according to an exemplary embodiment may include a controller 610 and an X-ray generator 620.

In detail, the X-ray apparatus 600 may identically correspond to the X-ray apparatus 100 described in FIG. 1. When the X-ray apparatus 600 identically corresponds to the X-ray apparatus 100, the controller 610 and the X-ray generator 620 identically correspond to the controller 150 and X-ray radiator 120 described in FIG. 1.

The controller 610 controls generation of an X-ray corresponding to a pulse signal including a plurality of pulses in which at least one of a pulse rate and a pulse amplitude varies. In detail, the controller 610 controls generation of a pulse-type X-ray which is generated by using the pulse signal. At least one of the image frames imaged by using the pulse type X-ray that passes through the object is adjusted. As described above, the pulse signal may be a pulse signal directly applied to the high voltage generator 121 or a control signal to control the high voltage signal applied to the high voltage generator 121. The term "adjustment may be used in a meaning including"correction and "interpolation". In detail, a term "image frame adjustment" may be used to include both of "correcting to increase quality of an image frame that actually exists" and "image frame interpolation to generate an virtual image frame that is not imaged by an actual shot of X-ray exposure and is generated by using at least one image frame that is imaged by the actual shot of X-ray exposure".

The X-ray generator 620 generates a pulse type X-ray under the control of the controller 610.

In detail, the controller 610 may control generation of a pulse signal including a plurality of pulses in which at least one of pulse rate and pulse amplitude varies. The controller 610 may control the X-ray generator 620 to generate a pulse type X-ray corresponding to the pulse signal.

Also, when the pulse type X-ray is radiated toward the object, the controller 610 may acquire a plurality of image frames by receiving data corresponding to the X-ray passing through the object and adjust the acquired image frames. The data corresponding to the X-ray passing through the object may be an electric signal detected by the detector 130 and may be a plurality of image frames imaged based on the electric signal detected from the detector 130.

Also, the X-ray apparatus 600 may be all image processing apparatuses that generate and process an X-ray image by receiving the data acquired by the X-ray apparatus 100, for example, the X-ray detected by the detector 130 or the electric signal acquired by the detected X-ray.

Also, the X-ray apparatus 600 may be all medical apparatuses that acquire and process an X-ray image by controlling the X-ray apparatus 100. For example, the X-ray apparatus 600 may identically correspond to the work station 110 of FIG. 1. In this case, the controller 610 and the X-ray generator 620 included in the X-ray apparatus 600 may be included in the controller 113 of FIG. 1. Also, when the X-ray apparatus 600 identically corresponds to the workstation 110, the X-ray generator 620 may generate a pulse signal to generate a pulse type X-ray and the controller 610 may control the pulse signal to be transmitted to the high voltage generator 121.

Figure 7:
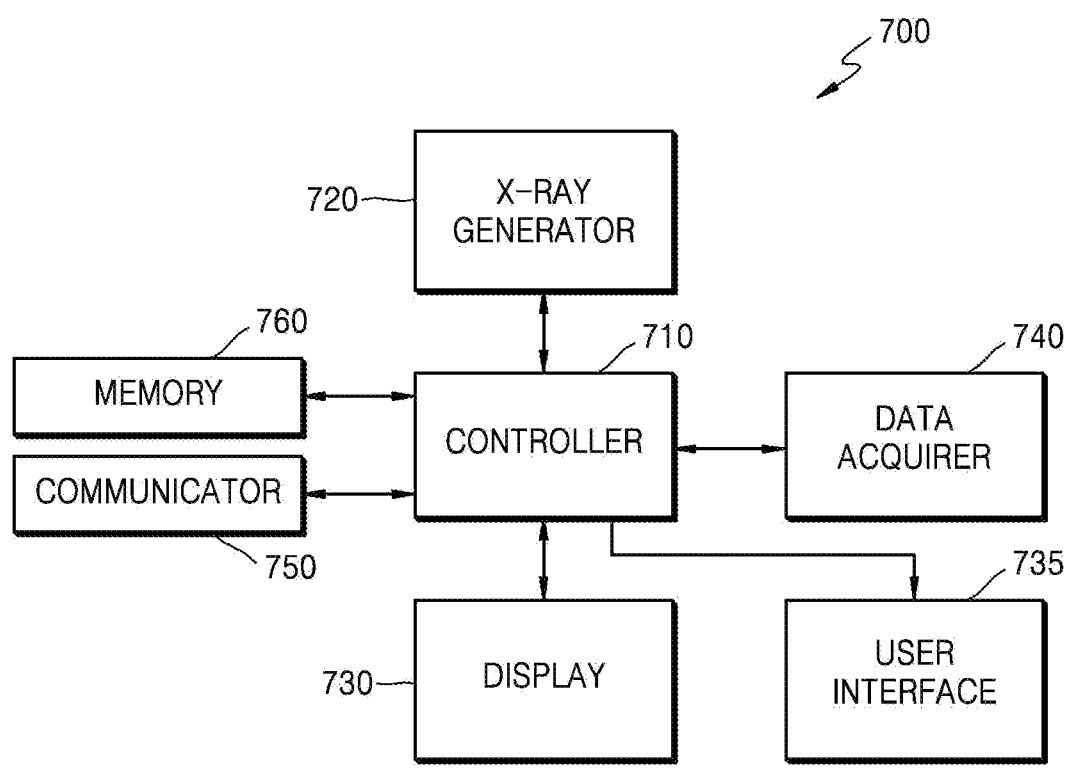
FIG. 7 is a block diagram of an X-ray apparatus according to another exemplary embodiment.

FIG. 7 is a block diagram of an X-ray apparatus 700 according to another exemplary embodiment. Since a controller 710 and an X-ray generator 720 included in the X-ray apparatus 700 according to another exemplary embodiment identically correspond to the controller 610 and the X-ray generator 620 of FIG. 6, redundant descriptions thereof are omitted.

Referring to FIG. 7, the X-ray apparatus 700 includes the controller 710 and the X-ray generator 720. The X-ray apparatus 700 may further include at least one of a display 730, a user interface 735, a data acquirer 740, a memory 750, and a communicator 760.

The controller 710 controls generation of a pulse type X-ray corresponding to a pulse signal including a plurality of pulses in which at least one of a pulse rate and a pulse amplitude varies.

In detail, the controller 710 may control at least one of a rate and an amplitude of a pulse signal based on a motion of the object. In detail, the controller 710 may control at least one of a rate and an amplitude of a pulse signal based on a target object included in the object.

The target object signifies a material other than human tissue, such as a guide wire, a syringe needle, a catheter, or a stent which is inserted into the object, as described above. The controller 710 may control at least one of a pulse rate and a pulse amplitude of a pulse signal, based on a motion of at least one of the object and the target object.

For example, when the object moves fast, an X-ray motion picture is generated to clearly show a change of the state of the object during a continuous time period. Accordingly, by maintaining a frame rate over a predetermined value, the X-ray motion picture formed by the image frames needs to express or show a change of the state of the object without interruption during a continuous time period. Thus, when the object moves fast, the controller 710 may generate the X-ray motion picture showing the motion of the object without interruption of an image without a decrease in the frame rate, based on the motion of the object.

As another example, when the object moves slowly, a change of the state of the object is generated slowly during a continuous time period. Accordingly, even at a low frame rate, the change of the state of the object may be expressed or shown without interruption during a continuous time period. Accordingly, when the object moves slowly, the controller 710 may decrease the frame rate based on the motion of the object.

The change of a state may signify at least one of changes in the position, shape, and pattern of at least one of the object and the target object which is generated due to the motion of at least one of the object and the target object.

In the pulse signal in which a frame rate varies, a frame rate value may be set to a value that is optimized through experiments. In detail, a frame rate at which the motion of the object may be expressed without interruption of an image according to a portion of the object may be obtained as an experimentally optimal value. Alternatively, a frame rate at which the motion of the target object may be expressed without interruption of an image based on a movement speed of the target object may be obtained as an experimentally optimal value.

Also, the frame rate according to the motion of the object and the target object may be set by the user.

Also, when the pulse amplitude is increased, a high amount of radiation of an X-ray is radiated. The high amount of radiation of an X-ray may further clearly image or increase the clarity of the object. When the object moves fast, the pulse amplitude may be maintained over a predetermined value to clearly image the object at a predetermined time point. Accordingly, when the object moves fast, the controller 710 may generate a pulse signal in which the pulse amplitude is not decreased, thereby clearly imaging the object.

In another example, when the object moves slowly, a change of the state of the object is generated slowly during a continuous time period. Accordingly, even when the pulse amplitude is decreased, the object may be clearly imaged at a predetermined time point. Thus, when the object moves slowly, the controller 710 may generate a pulse signal by decreasing the pulse amplitude, based on the motion of the object.

Also, the pulse amplitude may be set to be an experimentally optimal value similar to the setting the frame rate. Also, the pulse amplitude may be set by the user.

Also, when the target object inserted into the object is to be observed, at least one of the pulse rate and the pulse amplitude of a pulse signal may be set based on the motion of the target object.

In detail, at least one of the rate and the amplitude of a pulse signal may be controlled based on the movement speed of the target object.

For example, when the target object is a catheter and the object is a heart, a medical doctor needs to move the catheter to a target position in the heart while viewing a fluoroscopic image. The target position may be a predetermined position on a predetermined blood vessel into which a stent is inserted or a drug solution is injected using the catheter. When the catheter moves fast, the controller 710 may control such that at least one of the rate and the amplitude of a pulse signal does not decrease in order that the user may observe the motion of the catheter without interruption of an image.

The control and generation of a pulse signal according to the control of the controller 710 is described below in detail with reference to FIGS. 8 to 15.

Also, when the X-ray apparatus 700 corresponds to the workstation 110 of FIG. 1, the X-ray apparatus 700 may generate a pulse signal used to generate an X-ray or control the X-ray apparatus 100 to generate a pulse type X-ray corresponding to the pulse signal, instead of directly generating or radiating an X-ray. In detail, when the X-ray apparatus 700 corresponds to the workstation 110 of FIG. 1, the X-ray generator 720 may generate a pulse signal and transmit the pulse signal to the controller 150 of the X-ray apparatus 100 of FIG. 1. Alternatively, the X-ray generator 720 may control the controller 150 to generate a pulse type X-ray corresponding to a desired pulse signal.

Also, when the X-ray apparatus 700 corresponds to the X-ray apparatus 100 of FIG. 1, the X-ray apparatus 700 may directly generate and radiate an X-ray or generate a pulse type X-ray corresponding to the pulse signal. In detail, when the X-ray apparatus 700 corresponds to the X-ray apparatus 100 of FIG. 1, the X-ray generator 720 may generate a pulse signal according to the control of the controller 710. Alternatively, the X-ray generator 720 may generate a pulse type X-ray corresponding to the pulse signal according to the control of the controller 710.

The display 730 displays a predetermined screen. In detail, the display 730 may display at least one of image frames corresponding to at least one of pulses. The X-ray image may be an image frame acquired corresponding to a predetermined pulse. Also, the display 730 may display a fluoroscopic image that is an X-ray motion picture showing the object during a continuous time period. Also, the display 730 may display at least one of image frame and a fluoroscopic image on one screen. For example, the display 730 may display an X-ray image acquired as a result of X-ray imaging performed according to the control of the controller 710. In detail, the display 730 may display at least one of image frames that are acquired and adjusted corresponding to the pulse signal in which at least one of the pulse rate and the pulse amplitude varies.

Also, the display 730 may display a user interface screen. The user may input various settings and data for X-ray imaging by using the user interface screen output through the display 730.

Also, the display 730 may be all apparatuses through which the user may visually recognize predetermined data. For example, the display 730 may include a cathode ray tube (CRT) display, a liquid crystal display (LCD) display, a plasma display panel (PDP) display, an organic light-emitting display (OLED), an field emission display (FED), a light-emitting diode (LED) display, a VFD display, a digital light processing (DLP) display, a flat panel display (PFD), a 3D display, and a transparent display.

The user interface 735 generates and outputs a user interface screen to receive an input of a predetermined command or data from the user, and receives an input of a predetermined command or data from the user through the user interface screen. Also, the user interface screen output from the user interface 735 is output to the display 730. Then, the display 730 may display the user interface screen. The user may recognize predetermined information by viewing the user interface screen displayed through the display 730 and may input a predetermined command or data.

For example, the user interface 735 may include an input device including a mouse, a keyboard, or hard keys for inputting predetermined data. For example, the user may input predetermined data or a command by manipulating at least one of the mouse, the keyboard, or other input devices included in the user interface 735.

Also, the user interface 735 may be formed of a touchpad. In detail, the user interface 735 includes a touchpad (not shown) coupled to a display panel (not shown) included in the display 730, and outputs the user interface screen on the display panel. When a predetermined command is input through the user interface screen, the touchpad detects the predetermined command and, thus, the predetermined command input by the user may be recognized.

In detail, when the user interface 735 is formed of a touchpad, and the user touches a predetermined position on the user interface screen, the user interface 735 detects a touched position and may transmit detected information to the controller 710. Then, the controller 710 may recognize a user's request or command corresponding to a menu displayed at the detected position and may perform X-ray imaging or X-ray image generating operations by reflecting the recognized request or command.

In detail, the user interface 735 may provide the user interface screen for X-ray imaging or manipulation of the X-ray apparatus 700 to the user, for example, a radiologic technologist, or may receive a user's input of a command or various pieces of information for X-ray imaging or the manipulation of the X-ray apparatus 700.

In detail, the user interface 735 may receive a command to have a pulse type X-ray radiated toward the object.

Alternatively, the user interface 735, in response to a pulse signal, may receive a control command to change at least one of the pulse rate and the pulse amplitude. Then, the controller 710, in response to the control command, may generate a pulse signal to change at least one of the pulse rate and the pulse amplitude.

The data acquirer 740 acquires necessary data for the generation of an X-ray image. In detail, the data acquirer 740 may acquire a necessary electric signal for generation of an X-ray image, or an image frame. In detail, when the X-ray apparatus 700 corresponds to the workstation 110 of FIG. 1, the data acquirer 740 may receive from the X-ray apparatus 100 at least one of the image frames obtained by imaging the object by using the X-ray detected by the detector 130, the electric signal corresponding to the detected X-ray, and the detected X-ray. Also, when the X-ray apparatus 700 corresponds to the X-ray apparatus 100 of FIG. 1, the data acquirer 740 may correspond to the detector 130. The controller 710 may generate an X-ray image indicating the object, based on the data acquired by the data acquirer 740.

The memory 750 may store the data acquired according to the X-ray imaging. Also, the memory 750 may store various pieces of necessary data or programs for restoration of an X-ray image, or a finally acquired X-ray image or fluoroscopic image.

Also, the memory 750 may include at least one of storage mediums of a flash memory type, a hard disk type, a multimedia card micro type, a card type memory such as SD memory, XD memory, etc, random access memory (RAM), static RAM, read-only memory (ROM), electrically erasable programmable read-only memory (EEPROM), programmable read-only memory (PROM), magnetic memory, a magnetic disc, and an optical disc.

The communicator 760 may communicate with external devices, external medical apparatuses, etc. For example, the communicator 760 may be connected to at least one of an X-ray apparatus, a medical apparatus, a server, and a portable terminal which are externally connected. In detail, the communicator 760 is connected to an external X-ray apparatus and may receive necessary data for the generation of an X-ray image. Also, since the communicator 760 identically corresponds to the communicator (not shown) described with reference to FIG. 1, redundant descriptions thereof are omitted.

In detail, when the X-ray apparatus 700 corresponds to the work station 110 of FIG. 1, the communicator 760 may receive at least one of a plurality of image frames acquired in response to a pulse signal in which at least one of the pulse rate and the pulse amplitude from the X-ray apparatus 100 or the medical apparatus 164, and an electric signal to acquire the image frames. The communicator 760 may transmit the received image frames and the electric signal to acquire the image frames, to the controller 710. Then, the controller 710 may generate an X-ray image or a fluoroscopic image, based on the data received from the communicator 760.

In detail, the communicator 760 is connected to the network 15 of FIG. 1 in a wired or wireless manner and may perform communication with external devices, such as the server 162, the medical apparatus 164, or the portable terminal 166 of FIG. 1. The communicator 760 may exchange data with a hospital server or other medical apparatuses in a hospital connected via a picture archiving and communication system (PACS).

Also, the communicator 760 may perform data communication with external devices according to a digital imaging and communications in medicine (DICOM) standard.

The communicator 760 may transceive data related to diagnosis of the object through the network 15 of FIG. 1. Also the communicator 760 may transceive the medical image acquired by the medical apparatuses 164 of FIG. 1, such as an MRI apparatus, a CT apparatus, an X-ray apparatus.

Furthermore, the communicator 760 may receive a diagnostic history or treatment schedule of a patient from the server 162 of FIG. 1 and may be used for clinical diagnosis of the patient. Also, the communicator 760 may perform data communication not only with the server 162 or the medical apparatus 164 of FIG. 1 in the hospital, but also with the portable terminal 166 of FIG. 1 of the user or patient.

Also, the communicator 132 may transmit information about a device error, information about a quality control status, or the like to a system manager or a service manager via the network 301, and may receive a feedback regarding the information from the system manager or service manager.

In the following description, the operations of the X-ray apparatuses 600 and 700 according to the above-described exemplary embodiments are described below in detail with reference to FIGS. 8 to 15.

Figure 8:
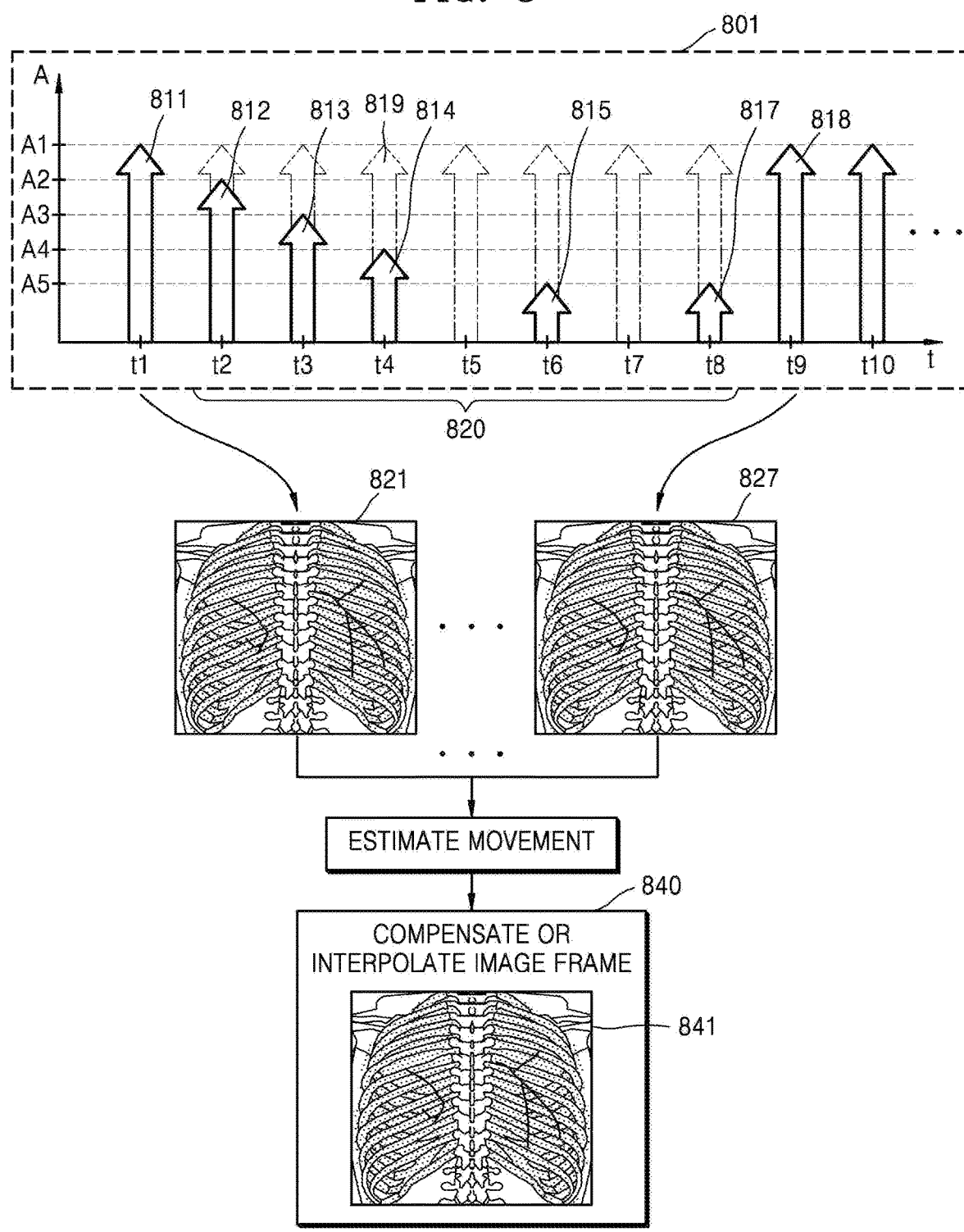
FIG. 8 is a view for describing an operation of an X-ray apparatus according to an exemplary embodiment.

FIG. 8 is a view for describing the operation of the X-ray apparatus 700 according to an exemplary embodiment. In the following description, the X-ray apparatus 700 of FIG. 7 is described as an example.

Referring to FIG. 8, the controller 710 controls generation of a pulse type X-ray corresponding to a pulse signal 801 including a plurality of pulses in which at least one of the pulse rate and the pulse amplitude varies.

In the graph indicating the pulse signal 801, the x-axis denotes time and the y-axis denotes amplitude of a pulse signal. It is assumed that a time interval between one time point, for example, t1, and another time point, for example, t2, that is adjacent to the time point t1 indicated on the graph, a time interval between the time point t2 and a time point t3, a time interval between the time point t3 and a time point t4, and so forth are all identical. Also, in the pulse signal 801, a pulse indicated by a dotted line, for example, pulse 819, denotes a reference pulse which may or may not be an actual pulse and in which the amplitude of a pulse signal has a predetermine value, whereas a pulse indicated by a solid line, for example, a pulse 814, denotes a pulse that is actually included in the pulse signal 801. Also, pulses indicated by solid lines 811, 812, 813, 814, 815, 817, and 818 denote pulses that are actually generated, whereas pulses indicated by dotted lines at t5 and t7 denote pulses that are not actually generated.

Also, the amplitude of the reference pulse may be the maximum amplitude of the pulse signal. Alternatively, the amplitude of the reference pulse may be set to a predetermined threshold value among the amplitude values that the pulse signal may have. The amplitude value of the reference pulse may be set in consideration of the product specifications of the X-ray apparatus 700, the quality of an X-ray image, a human body portion to be imaged, a target object to be imaged, etc. For example, when the minimum amplitude of a pulse for the quality of an X-ray image to have a level of an image quality demanded by the user is A1, the amplitude of the reference pulse may be set to A1. In the pulse signal 801 of FIG. 8, an example in which the amplitude of the reference pulse is A1 is illustrated.

In detail, if a pulse signal generated before the controller 710 varies the pulse rate and the pulse amplitude has the shape illustrated in FIG. 5, the controller 710 may generate the pulse signal 801 by varying at least one of the pulse rate and the pulse amplitude like the pulse signal 801 illustrated in FIG. 8.

Referring to FIG. 8, the pulse signal 801 includes a first pulse 811 having an amplitude of A1 at a time point t1, a second pulse 812 having an amplitude of A2 at a time point t2, a third pulse 813 having an amplitude of A3 at a time point t3, a fourth pulse 814 having an amplitude of A4 at a time point t4, a sixth pulse 815 having an amplitude of A5 at a time point t6, an eighth pulse 817 having an amplitude of A5 at a time point t8, and a ninth pulse 818 having an amplitude of A1 at a time point t9. Also, in the pulse signal 801, no pulse is generated at time points t5 and t7. In other words, the controller 710 may vary the pulse amplitude value at the time points t2, t3, t4, t6, and t8, and may vary the pulse rate of the pulse signal 801 such that no pulse is generated at the time points t5 and t6.

When an X-ray corresponding to one pulse is radiated toward the object, the controller 720 images one image frame by detecting the X-ray that passes through the object. Accordingly, a plurality of image frames 821 to 827 may be respectively imaged corresponding to the pulses 811, 812, 813, 814, 815, 817, and 818 included in the pulse signal 801.

Also, the pulse signal may include a first section including at least one pulse and a second section including at least one pulse. The controller 710 may adjust at least one image frame corresponding to at least one pulse included in the second section, based on an image frame corresponding to at least one reference pulse included in the first section. The first section may be a section in which the pulse rate and the pulse amplitude are not varied. In detail, the first section may be a section including at least one reference pulse, that is, a time section other than a second section 820. The second section 820 may be a section in which at least one of the pulse rate and the pulse amplitude is varied.

The controller 710 may adjust the image frames corresponding to time points included in the second section 820. For example, the controller 710 may adjust at least one image frame corresponding to at least one pulse among the pulses 812, 813, 814, 815, and 817 included in the second section 820, based on the image frame 821 corresponding to the reference pulse, for example, the pulse 811, included in the first section. The adjustment of the image frame is described below in detail with reference to FIG. 9A.

In detail, the first section that is the time section other than the second section 820 includes at least one pulse that is applied while the target object moves through a first portion of the object. The second section 820 includes at least one pulse that is applied while the target object moves through a second portion that moves slower than through the first portion. The object may be a heart and the target object may move toward a cardiovascular vessel included in the heart. In detail, the first portion is a region of the object including a first blood vessel, and the second portion is a region of the object including a second blood vessel which is thinner than the first blood vessel. In detail, the first portion may be an area of the object including a relatively thick blood vessel and the second portion may be an area of the object including a relatively thin blood vessel.

When the object is a catheter, the catheter moving through a relatively thick cardiovascular vessel moves faster than the catheter moving through a relatively thin cardiovascular vessel. When the target object moves fast, the state of the object including the target object changes much during a predetermined time interval, for example, an interval between the time point t1 and the time point t2. Accordingly, X-ray imaging may be performed without decreasing the pulse rate while the target object moves fast. Also, when the target object moves slowly, the state of the object including the target object changes less during the predetermined time interval. Accordingly, even when X-ray imaging is performed as the X-ray apparatus 700 decreases the pulse rate while the target object moves slowly, an image interruption phenomenon may occur less in a finally acquired fluoroscopic image. Also, when the target object moves slowly, motion artifacts are generated less in the X-ray image. Accordingly, even when the X-ray apparatus 700 performs the X-ray imaging by decreasing the pulse amplitude, the motion artifacts may be adjusted by subsequent X-ray image adjustment.

Accordingly, the controller 710 may control at least one of the pulse rate and the pulse amplitude, according to the portion of the object where the target object moves or according to the movement speed of the target object.

Also, the controller 710 may control such that each of the pulse rate and amplitude of at least one pulse included in the second section 820 has a value equal to or less than the pulse rate and amplitude of at least one pulse included in the first section that is the time section other than the second section 820. In detail, the controller 710 may control such that the amplitude of at least one pulse included in the second section 820 is equal to or less than the amplitude of the reference pulse 811. Also, the controller 710 may control such that the pulse rate of the second section 820 is equal to or less than the pulse rate of the first section that is the time section other than the second section 820.

Also, the controller 710 may generate at least one interpolated image frame located between the image frames, based on at least one of the image frames corresponding to the pulses included in the pulse signal 801. In detail, the controller 710 may generate at least one interpolated image frame, for example, an image frame corresponding to the time point t5 and/or an image frame corresponding to the time point t7, based on at least one of the image frames 821 to 827 respectively corresponding to the pulses 811, 812, 813, 184, 815, 816, and 817 included in the pulse signal 801. The interpolation of the image frame is described below in detail with reference to FIG. 10.

In detail, the controller 710 may estimate at least one of the movement and the shape of the object at a predetermined time point, based on at least one of the image frames 821 to 827 respectively corresponding to the pulses 811, 812, 813, 814, 815, 817 and 818 included in the pulse signal 801, and motion information indicating a movement of the object, and may perform at least one of the image frame adjustment operation and the image frame interpolation operation based on the anticipation (Operation in Block 840).

Figure 9A:
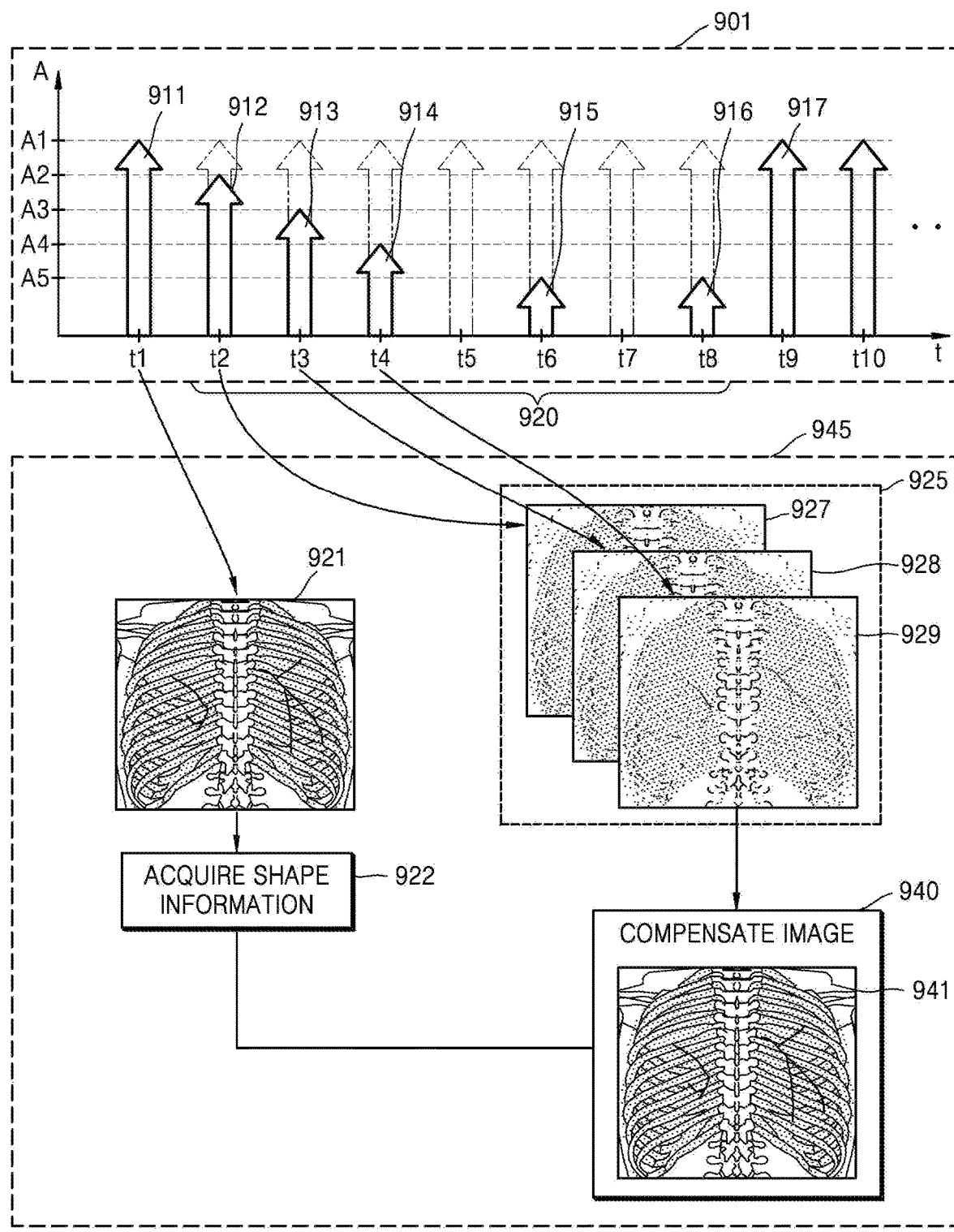
FIG. 9A is a view for describing an operation of an X-ray apparatus according to another exemplary embodiment.

FIG. 9A is a view for describing an operation of the X-ray apparatus 700 according to another exemplary embodiment. Since a pulse signal 901 of FIG. 9A identically corresponds to the pulse signal 801 of FIG. 8, redundant descriptions thereof are omitted.

The controller 710 may acquire shape information indicating the object at at least one time point, and may adjust at least one of a plurality of image frames based on the shape information.

Referring to FIG. 9A, the controller 710 acquires a reference image frame 921 that is an image frame corresponding to a reference pulse 911. The controller 710 may acquire shape information indicating an anatomical structure of the object from the object included in the reference image frame 921 (Operation in Block 922). The shape information is used for adjusting the image frame that is imaged at a predetermined time point. A detailed portion of the object presented in the image frame may be adjusted based on the shape information. For example, the controller 710 may adjust a detailed portion of the object in the image frame based on the shape information, so that motion artifacts generated due to a movement are reduced.

In detail, the shape information may indicate surfaces included in the object, and may indicate an edge in the image frame that images the object. For example, the shape information may include at least one of a feature map indicating the shape of the object and an edge map indicating a surface included in the object.

In detail, the controller 710 may adjust at least one of image frames 925 corresponding to at least one of pulses included in the second section 920, based on the shape information acquired from the reference image frame 921 (Operation in Block 940). In the following description, for convenience of explanation, an image frame 941 that is adjusted based on the shape information acquired based on the reference image frame 921 may be referred to as the adjusted image frame 941. Also, in the operation in Block 940, for example, an image frame generated by correcting at least one of the image frames 925 corresponding to an actual pulse may be referred to as the corrected image frame. The correction of an image frame may include any image processing to improve the quality of an image frame. For example, the correction of an image frame may include image processing such as edge enhancement, noise reduction, contrast enhancement, etc.

The reference pulse 911 is a pulse having the maximum pulse amplitude as described above. Accordingly, the reference image frame 921 acquired corresponding to the reference pulse 911 may be an image frame acquired through radiating a high amount radiation onto the object and may be an image frame obtained clearly imaging the object. Accordingly, the reference image frame 921 may be an image frame obtained clearly imaging a detailed portion of the object including the shape of the object. When the shape information is acquired from the reference image frame 921, the shape of the object may be accurately identified.

The controller 710 may estimate the shape of the object at an image frame to be adjusted, for example, an image frame 929 at the time point t4, by applying a movement of the object to the shape information acquired from the reference image frame 921. For example, the controller 710 may acquire an edge map indicating the object at the time point t1 by using the reference image frame 921, and apply an amount of movement of the object occurring between the time point t1 to the time point t4 to the edge map indicating the object at the time point t1, thereby acquiring the edge map indicating the object at the time point t4. The controller 710 adjusts the image frame 929 to be adjusted, based on the edge map indicating the object at the time point t4. Then, the controller 710 may acquire the adjusted image frame 941 corresponding to the time point t4, which further clearly images the target object and the object.

Also, the controller 710 may acquire an image frame (not shown) having reduced noise corresponding to the time point t4, by performing image fusion on the image frame 929 corresponding to the time point t4, which is the image frame to be adjusted, and at least one of image frame corresponding to at least one of the time points before the time point t4, for example, an image frame 927 corresponding to the time point t2 and an image frame 928 corresponding to the time point t3. The controller 710 may acquired the adjusted image frame 941 corresponding to the time point t4, by adjusting an image frame (not shown) corresponding to the time point t4 and acquired through the image fusion, based on the edge map indicating the object at the time point t4.

FIG. 9A illustrates an example in which the controller 710 acquires an image frame (not shown) indicating the object at the time point t4, by performing image fusion on three image frames with respect to the time point t4, that is, the image frame 927 acquired at the time point t2, the image frame 928 acquired at the time point t3, and the image frame 929 acquired at the time point t4. However, the number and time points of the image frames used for the image fusion may vary. In another example, an image frame (not shown) indicating the object at the time point t4 may be acquired by performing image fusion on two image frames with respect to the time point t4, that is, the image frame 928 acquired at the time point t3 and the image frame 929 acquired at the time point t4.

The adjustment of an image frame based on the shape information is described below in detail with reference to FIG. 9B.

Figure 9B:
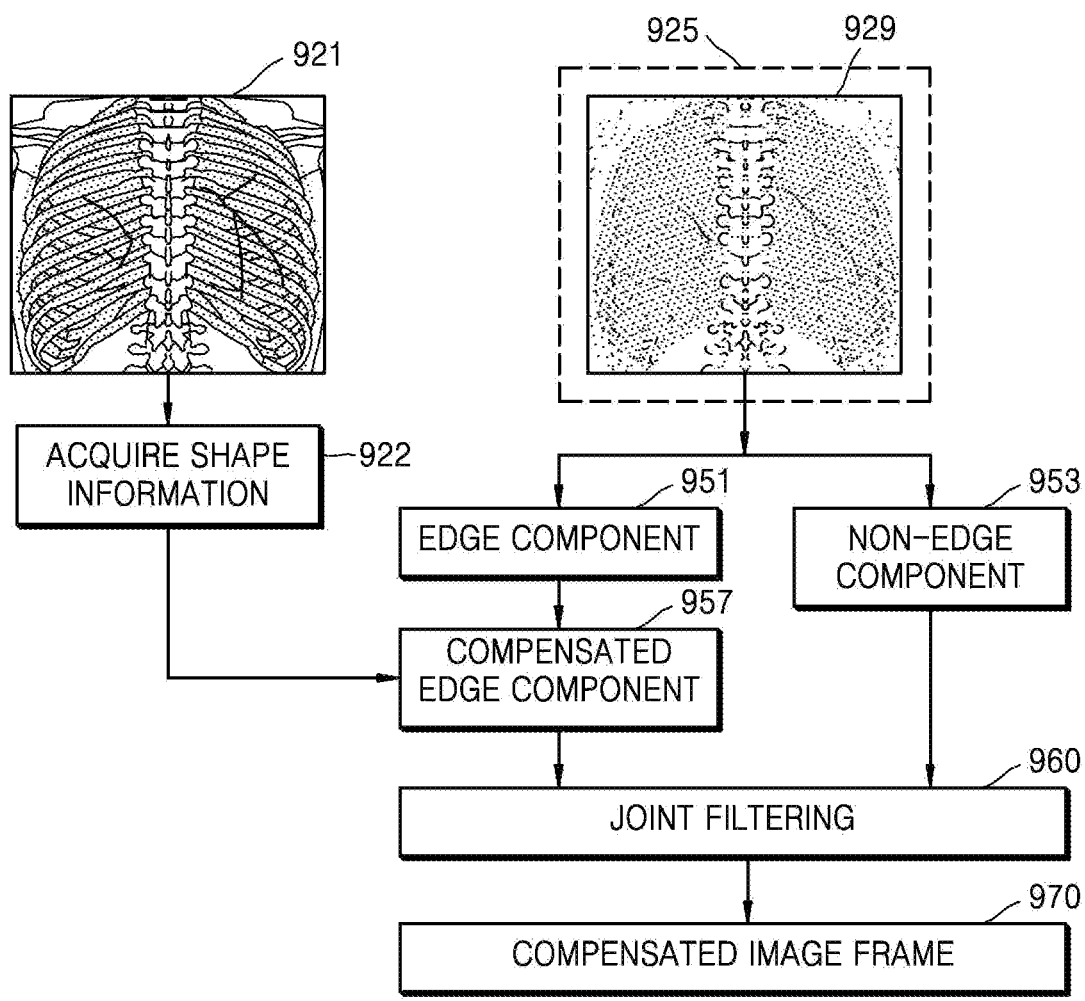
FIG. 9B illustrates in detail an image frame adjustment operation.

FIG. 9B illustrates in detail an image frame adjustment operation. In detail, FIG. 9B illustrates the image frame adjustment performed by the controller 710. Since the same elements in FIGS. 9A and 9B are illustrated by using the same reference numerals, redundant descriptions thereof are omitted.

Referring to FIG. 9B, as described above in FIG. 9A, the controller 710 acquires the shape information indicating the object at a time point, for example, t4, when the adjustment is performed based on the reference image frame 921 (Operation in Block 922). For example, an edge map is acquired from the reference image frame 921 indicating the object at the time point t1, and the edge map at the time point t1 may be transformed to an edge map at the time point t4 by reflecting the movement of the object occurring between the time point t1 and the time point t4.

The controller 710 may adjust the image frame 929 corresponding to a predetermined time point, for example, the time point t4, which is subject to the adjustment, based on the edge map indicating the object at a predetermined time point, for example, the time point t4. The image frame 929 to be adjusted may be an image frame imaged by the pulse 914 output at a predetermined time point, for example, the time point t4, or an image generated by the image fusion described in FIG. 9A.

In the following description, for convenience of explanation, the image frame 929 to be adjusted may be referred to as the before-adjustment image frame 929.

The controller 710 may decompose the before-adjustment image frame 929 into an edge component 951 and a non-edge component 953. The non-edge component 953 is a component excluding the edge component 951 from the before-adjustment image frame 929 and may include a brightness component indicating shading of an image. The controller 710 may adjust the edge component 951 based on the edge map. In detail, the controller 710 may adjust the image frame acquired at the time point t4 or the image frame corresponding to the time point t4 that is generated through the image fusion, based on the edge map indicating the object at the time point t4 acquired based on the reference image frame 921.

In detail, the controller 710 may transform the edge component 951 according to the edge map indicating the object at a predetermined time point, for example, the time point t4. Alternatively, the controller 710 may acquire an adjusted edge component 957 by transforming the edge component 951 with an average value of the edge component 951 and the edge map indicating the object at a predetermined time point, for example, the time point t4.

The controller 710 may acquire an adjusted image frame 970 based on the adjusted edge component 957 and the non-edge component 953. For example, the controller 710 may acquire the adjusted image frame 970 that is an image frame corresponding to a predetermined time point, for example, the time point t4, and having an improved edge, by performing joint filtering on the adjusted edge component 957 and the non-edge component 953. Alternatively, the controller 710 may acquire the adjusted image frame 970 by compositing the adjusted edge component 957 and the non-edge component 953.

Referring back to FIG. 9A, the controller 710 may adjust at least one of the image frames corresponding to at least one of the pulses included in the second section, based on the reference image frame 921, in the above-describe method.

Also, the controller 710 may adjust a second image frame (not shown) imaged by the second pulse 912 output at the subsequent time point t2, based on the reference image frame 921 imaged by the first pulse 911 output at the time point t1. Also, the controller 710 may adjust a third image frame (not shown) imaged by the third pulse 913 output at the subsequent time point t3, based on a adjusted second image frame 921 (not shown). Also, the controller 710 may adjust a fourth image frame (not shown) imaged by the fourth pulse 914 output at the subsequent time point t4, based on a adjusted third image frame (not shown).

Also, the controller 710 may finally acquire the adjusted image frame 941 by performing image fusion on the image frames adjusted as described above. For example, the second image frame (not shown) imaged by the second pulse 912 output at the subsequent time point t2 is adjusted based on the reference image frame 921 imaged by the first pulse 911 output at the time point t1. The third image frame imaged by the third pulse 913 output at the subsequent time point t3 is adjusted based on the adjusted second image frame imaged. An adjusted image frame (not shown) corresponding to the time point t3 may be acquired by performing image fusion on the adjusted second image frame and the adjusted the third image frame.

Also, as described above, after acquiring an image frame corresponding to a predetermined time point by performing image fusion on the adjusted image frames, the controller 710 may adjust an image-fusion image frame based on an edge map at a predetermined time point acquired based on the reference image frame 921. In other words, the controller 710 may acquire an image frame obtained by performing image fusion on the adjusted image frames, based on the edge map, and may finally acquire the adjusted image frame 941.

In the following description, a case in which the X-ray apparatus 700 acquires a plurality of image frames by using a pulse signal in which a pulse amplitude is not changed and only pulse rate varies is described below in detail with reference to FIG. 10. Also, a case in which the X-ray apparatus 700 acquires a plurality of image frames by using a pulse signal in which pulse rate is not changed and only pulse amplitude varies is described below in detail with reference to FIG. 11. Also, a case in which the X-ray apparatus 700 acquires a plurality of image frames by using pulse signal in which both a pulse amplitude and a pulse rate vary is described below in detail with reference to FIG. 12.

Figure 10:
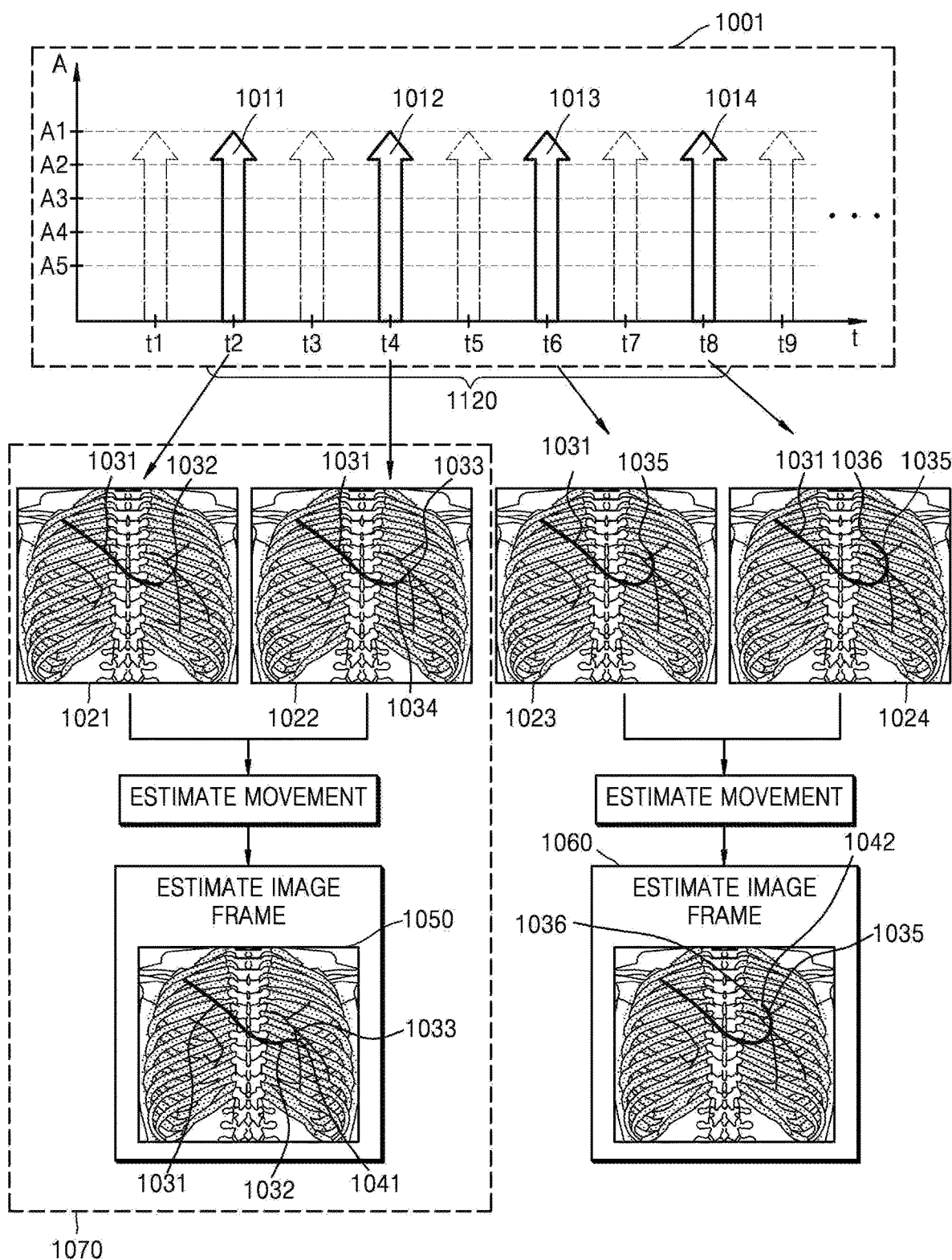
FIG. 10 is a view for describing an operation of an X-ray apparatus according to another exemplary embodiment.

FIG. 10 is a view for describing an operation of the X-ray apparatus 700 according to another exemplary embodiment.

The controller 710 may control generation of a pulse signal 1001 in which pulse rate varies.

Referring to FIG. 10, a pulse indicated by a dotted line is not a pulse that is output and only a pulse indicated by a solid line is one that is actually output. The pulse signal 1001, compared to the pulse signal illustrated in FIG. 5A, has a variable pulse rate so that no pulse is generated at the time points t1, t3, t5, t7, and t9. The pulse signal 1001 has pulses 1011, 1012, 1013, and 1014 output only at the time points t2, t4, t6, and t8. Accordingly, the controller 710, compared to the pulse signal illustrated in FIG. 5A, may generated a pulse signal 1001 having a pulse rate that is reduced to ½. Also, the controller 710 may generate the pulse signal 1001 only in the second time section that is a time section from the time point t1 to the time point t9, and may generate a pulse signal (not shown) having a pulse rate that is not reduced in the first time section that is the other time section.

The X-ray passing through the object may be detected only at the time point when a pulse is output. Accordingly, an image frame is imaged only at the time point when a pulse is output. Accordingly, when the pulse rate is reduced, the image frame may not be actually imaged at the time point when the pulse is output and thus the image interruption phenomenon may occur in the fluoroscopic image. Thus, in the X-ray apparatus 700 according to an exemplary embodiment, although the pulse rate decreases, the frame rate is not reduced. In detail, the X-ray apparatus 700 may generate an image frame corresponding to the time point when no actual pulse is output, through the image frame interpolation such that, even when the pulse rate is reduced, no interruption phenomenon may occurs in an X-ray motion picture.

In detail, the X-ray apparatus 700 may operate as follows.

The X-ray generator 720 may generate a pulse type X-ray corresponding to a pulse signal including a plurality of pulses and a varying pulse rate and radiate the pulse type X-ray toward the object, according to the control of the controller 710.

The controller 710 may acquire a plurality of final image frames having a frame rate larger or higher than the pulse rate of the pulse signal, based on a plurality of image frames imaged based on the pulse type X-ray.

In detail, the controller 710 may acquire at least one of interpolation frames located between the first image frame and the second image frame, based on a first image frame corresponding to a first time point and a second image frame corresponding to a second time point adjacent to the first time point.

Referring to FIG. 10, an image frame 1021 is imaged based on a pulse 1011 output at the time point t2, and an image frame 1022 is imaged based on a pulse 1012 output at the time point t4. Then, an image frame 1023 is imaged based on a pulse 1013 output at the time point t6, and an image frame 1024 is imaged based on a pulse 1014 output at the time point t8.

The controller 710 may interpolate at least one image frame 1050 located between the time point t2 and the time point t4, based on the image frame 1021 corresponding to the pulse 1011 output at the time point t2 and the image frame 1022 corresponding to the pulse 1012 output at the time point t4 which is a pulse output adjacent to the pulse 1011. For example, the image frame 1050 corresponding to the time point t3 that is a middle time point between the time point t2 and the time point t4 by averaging the image frame 1021 and the image frame 1022.

Also, the controller 710 may acquire motion information that is information about a movement of the object, and may generate an interpolation frame corresponding to a time point when no actual pulse is output, based on the motion information.

In detail, the controller 710 acquires motion information of the object. Then, the controller 710 may generate at least one interpolated image frame corresponding to a time point when no actual pulse is output, based on the acquired motion information and at least one of a plurality of image frames corresponding to at least one time point when a pulse is actually output. In detail, the controller 710 may acquire the motion information of the object, for example, a heart, including a target object 1031, and may generate an interpolation frame corresponding to the time point when no actual pulse is output based on the motion information and at least one image frame corresponding to the actual output pulse.

The controller 710 may acquire motion information of the object in a continuous time section. The object may be an object including the target object 1031. Also, motion information is information indicating a movement of the object according to time and may be information indicating a change in an imaged edge in a surface or an image frame of the object according to time.

In detail, the motion information may be measured by using a variety of motion measurement techniques such as block matching, feature matching, non-rigid registration, rigid registration, optical flow, etc.

The block matching is a technique of calculating a change amount between images by matching the images for each predetermined block included in consecutive image frames according to a time change. In detail, in the consecutive image frames, a sum of square differences (SSD) value may be measured and a movement amount between the consecutive image frames may be measured based on the measured value. The controller 710 may acquire motion information indicating a movement of the object according to time based on the measured SSD value.

Also, instead of the SSD value, a value indicating a signal difference included in an image, such as a sum of absolute differences (SAD), a mean of absolute differences (MAD), a signal to noise ratio (SNR), a mean square error (MSE), a peak signal to noise ratio (PSNR), or a root mean square error (RMSE), is measured and the movement amount between the consecutive image frames may be measured based on the measured value.

Also, the controller 710 may acquire a motion vector field (MVF) indicating a movement of the object, as the motion information. The MVF may be acquired through a method, such as non-rigid registration or rigid registration. In detail, according to the non-rigid registration method, a plurality of control points are set in each image frame, for example, the image frame 1022, adjacent to one image frame, for example, the image frame 1021, and an optimal motion vector at each control point is calculated. The motion vector is a vector including the direction and movement distance of a movement. The MVF indicating the motion vectors in all voxels included in an image frame is obtained by interpolating motion vectors at each control point.

Also, the controller 710 may acquire motion information through the feature matching technique. In detail, a plurality of control points are set in the object at each image frame, for example, the image frame 1022, adjacent to one image frame, for example, the image frame 1021, and the control points indicating the same point of the object are compared with each other, thereby obtaining a motion vector. In detail, a relative difference value between the control points is obtained by matching the control points. The relative difference value may be used as a motion vector at a current control point. A motion vector field indicating motion vectors in all voxels included in an image frame may be created by interpolating motion vectors at the respective control points.

As described above, the controller 710 may acquire motion information indicating a movement of the object according to time. The controller 710 may estimate the movement of the object at a time point when an interpolated frame is acquired or produced, based on the motion information. The controller 710 may interpolate the image frame 1050 corresponding to a predetermined time point, for example, the time point t3, based on the movement of the object at the predetermined time point, for example, the time point t3, when the interpolated frame is acquired.

Also, the controller 710 may acquire the motion information of the object and may generate at least one interpolated image frame based on the acquired information and at least one of a plurality of image frames. For example, the controller 710 may primarily interpolate the image frame corresponding to the time point t3 by averaging one image frame, for example, the image frame 821, and an image frame adjacent thereto, for example, the image frame 822, and may adjust the primarily interpolated image frame corresponding to the time point t3 based on the motion information. In detail, the primarily interpolated image frame corresponding to the time point t3 is motion-adjusted based on the movement amount of the object at the time point t3 indicated by the motion information, and thus, an interpolated image frame 850 that more accurately reflects the state of the object at the time point t3 may be finally acquired or provided.

The controller 710 may generate motion information directly from a plurality of image frames acquired corresponding to a plurality of pulses. Also, the controller 710 may externally receive the motion information through the communicator 760.

Referring to FIG. 10, the target object 1031 moves according to time. In detail, it may be seen that an end of the target object 1031 imaged at the image frame 1021 corresponding to the time point t2 is located at a first position 1032, and an end of the target object 1031 imaged at the image frame 1022 corresponding to the time point t4 is located at a second position 1033. Also, it may be seen that an end of the target object 1031 presented in the interpolated image frame 1050 acquired corresponding to the time point t3 through the above-described image interpolation is located at a third position 1041 between the first position 1032 and the second position 1033. Accordingly, when a fluoroscopic image is acquired by arraying the image frame 1021, the interpolated image frame 1050, and the image frame 1022 in order of time, the image interruption phenomenon is reduced and, thus, a more natural real-time X-ray motion picture may be obtained.

Also, the target object 1031 continuously moves according to time. In detail, it may be seen that an end of the target object 1031 imaged at the image frame 1023 corresponding to the time point t6 is located at a fourth position 1035, and an end of the target object 1031 imaged at the image frame 1024 corresponding to the time point t8 is located at a fifth position 1036. Also, it may be seen that an end of the target object 1031 presented at the interpolated image frame 1080 acquired corresponding to the time point t7 through the above-described image interpolation is located at a sixth position 1042 between the fourth position 1035 and the fifth position 1036. Accordingly, when a fluoroscopic image is acquired by arraying the image frame 1023, the interpolated image frame 1060, and the image frame 1024 in order of time, the image interruption phenomenon is reduced and, thus, a more natural X-ray motion picture may be obtained.

The controller 710 may acquire a plurality of final image frames based on at least one interpolated image frame and a plurality of image frames corresponding to a plurality of actually output pulses, as described above. A fluoroscopic image may be provided by arraying the final image frames in order of time.

Also, the controller 710 may adjust the pulse rate of a pulse signal based on the movement of the target object 1031 in the object. As described above, the pulse rate may be set to be a value proportional to a movement speed of the target object 1031. For example, the controller 710 may increase the pulse rate when the movement of the target object 1031 is fast and may decrease the pulse rate when the movement of the target object 1031 is slow.

Also, the controller 710 may adjust the number of the interpolated image frames based on the movement of the target object 1031 in the object. In detail, when the target object 1031 moves fast, a frame rate may be increased to generate more natural fluoroscopic image. Accordingly, when the target object 1031 moves fast, the controller 710 may increase the number of the interpolated image frames. For example, although FIG. 10 illustrates an example in which one interpolated image frame 1050 is generated between the time point t2 and the time point t4 when pulses are actually output, two or more interpolated image frames (not shown) are controlled to be generated between the time point t2 and the time point t4 when pulses are actually output.

As described above, the X-ray apparatus 700 may decrease the amount of X-ray by decreasing the pulse rate. Also, even when the pulse rate is decreased, the frame rate may be increased over the pulse rate through the image interpolation, the image interruption phenomenon in a fluoroscopic image may be reduced. Also, the X-ray apparatus 700 acquires the motion information of the object and adjusts the interpolated frame image based on the motion information and thus a fluoroscopic image which accurately reflects the movement of the target object 1031 may be provided.

Figure 11:
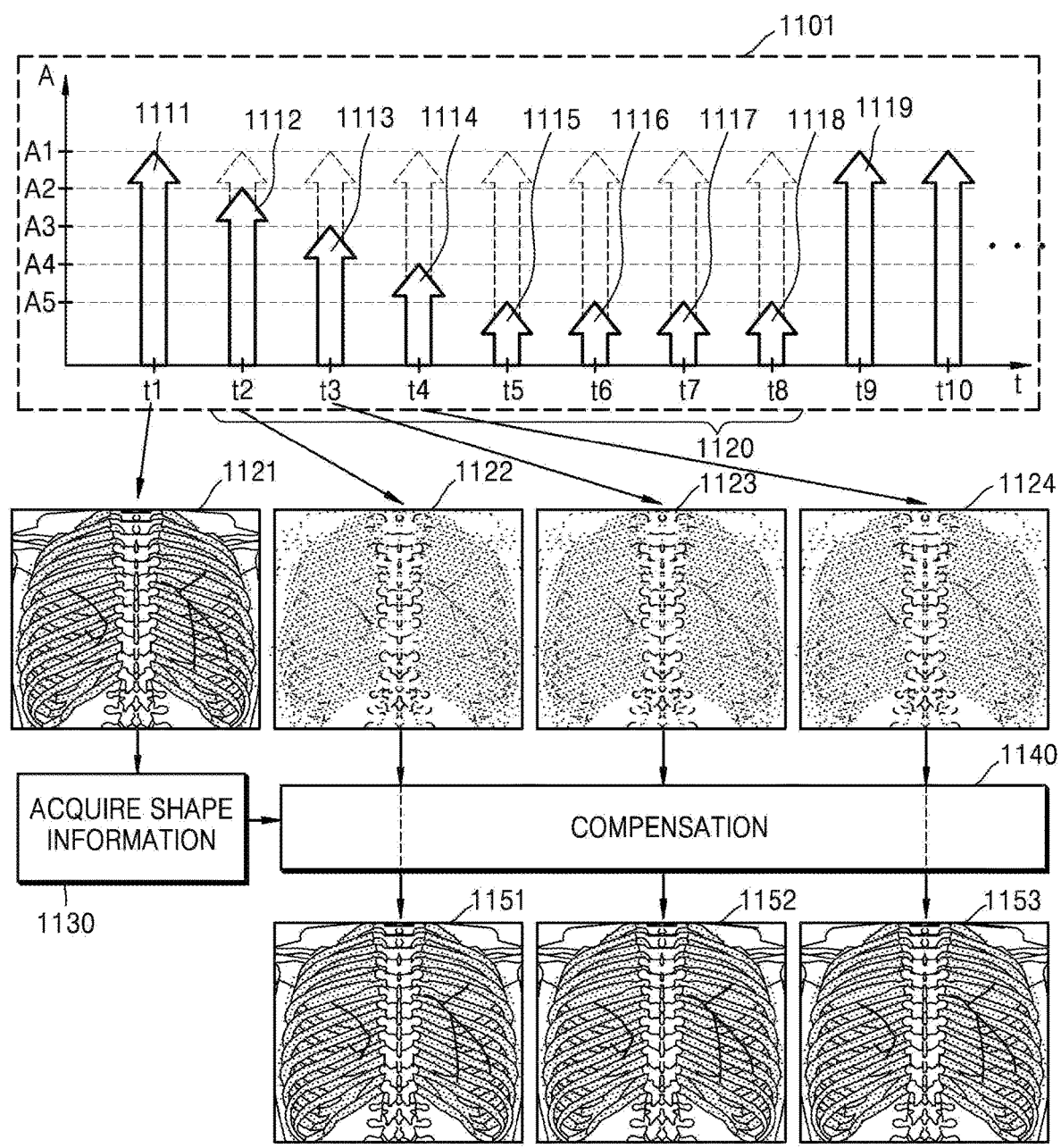
FIG. 11 is a view for describing an operation of an X-ray apparatus according to another exemplary embodiment.

FIG. 11 is a view for describing an operation of the X-ray apparatus 700 according to another exemplary embodiment.

The controller 710 may control the generation of the pulse signal 1001 in which a pulse amplitude varies.

In detail, the X-ray apparatus 700 may operate as follows.

The X-ray generator 720 generates a pulse type X-ray corresponding to a pulse signal including a plurality of pulses and having a varying pulse amplitude and radiates the generated pulse type X-ray toward the object.

The controller 710 adjusts at least one of a plurality of image frames based on at least one reference image frame of the image frames imaged based on the pulse type X-ray.

In detail, the controller 710 may acquire shape information indicating the object at at least one time point based on at least one reference image frame, and may adjust at least one of the image frames based on the shape information.

Referring to FIG. 11, a pulse signal 1101 includes a plurality of pulses 1111 to 1119 output at a predetermined interval. In FIG. 11, an example of the pulse signal 1101 in which the pulse rate is constant and only the pulse amplitude varies is illustrated.

Also, referring to FIG. 11, an example in which the pulse amplitude varies in the second section 1120 including the time point t2 to the time point t8 and remains constant in the other section is illustrated.

In detail, an example in which the pulse signal 1101 includes a reference pulse 1111 and a first pulse 1112 adjacent to the reference pulse 1111 and having a relatively decreased amplitude compared to that of the reference pulse 1111 is illustrated. In detail, the pulse signal 1101 includes at least one of the pulses 1112, 1113, 1114, 1115, 1116, 1117, and 1118 having an amplitude that is smaller than the amplitude A1 of the reference pulse 1111 in a first section 1120. The controller 710 may generate an adjusted image frame 1151 by adjusting a first image frame 1122 corresponding to the first pulse 1112 based on a reference image frame 1921 corresponding to the reference pulse 1111.

The image frame adjustment of the controller 710 is described below in detail.

In FIG. 11, the image frame 1121 indicates an image frame imaged by the pulse type X-ray corresponding to the reference pulse 1111 output from the time point t1, and the image frame 1122 corresponds to an image frame imaged by the pulse type X-ray corresponding to the first pulse 1112 output at the time point t2. The image frame 1123 corresponds to an image frame imaged by the pulse type X-ray corresponding to the pulse 1113 output at the time point t3. The image frame 1124 corresponds to an image frame imaged by the pulse type X-ray corresponding to the pulse 1114 output at the time point t4.

Also, the image frames 1121, 1122, 1123, and 1124 are not the finally adjusted image frames. For example, the image frame 1122 may be an image frame imaged by the pulse type X-ray corresponding to the pulse 1112 output at the time point t2. Also, the image frame 1122 may be an image acquired by performing image fusion on at least one of the image frames acquired before or at the time point t2. Also, the image frame 1123 may be an image frame imaged by the pulse type X-ray corresponding to the pulse 1113 output at the time point t3. Also, the image frame 1123 may be an image acquired by performing image fusion on at least one of the image frames acquired before or at the time point t3. In the following description, an example in which the image frames 1122, 1123, and 1124 are image frames imaged by pulses output at corresponding time points is described.

The image frame 1151 is an adjusted image frame that is finally acquired or produced by adjusting the image frame 1122. An image frame 1152 is an adjusted image frame that is finally acquired or produced by adjusting the image frame 1123. Also, an image frame 1153 is an adjusted image frame that is finally acquired or produced by adjusting the image frame 1124.

In detail, the controller 710 acquires the shape information indicating the object at at least one time point based on at least one reference image frame, for example, the reference image frame 1121 (Operation in Block 1130). Since the acquisition of the shape information (Operation in Block 1130) is the same as that described with reference to FIG. 9A (Operation in Block 922), redundant descriptions thereof are omitted. The controller 710 adjusts an image frame based on the shape information (Operation in Block 1140). Since the image frame adjustment (Operation in Block 1140) is the same as that described with reference to FIG. 9 (Operation in Block 940), redundant descriptions thereof are omitted.

In detail, the controller 710 acquires or produces the adjusted image frame 1151 by adjusting the image frame 1122 based on the shape information, for example, the edge map, of the object at a predetermined time point acquired based on the reference the image frame 1121. In the following description, the edge map is described as an example of the shape information of the object.

Also, the controller 710 acquires an edge map from the adjusted image frame 1151. Since the edge map acquired from the adjusted image frame 1151 is the shape information indicating the object at the time point t2, the edge map acquired from the adjusted image frame 1151 is transformed to an edge map indicating the object at the time point t3. The adjusted image frame 1152 is acquired by adjusting the image frame 1122 based on the transformed edge map that is the edge map indicating the object at the time point t3.

Next, the controller 710 acquires an edge map indicating the shape of the object at the time point t3 based on the adjusted image frame 1152. The edge map acquired from the adjusted image frame 1152 is transformed to an edge map indicating the object at the time point t4. The adjusted image frame 1153 is acquired or produced by adjusting the image frame 1124 based on the transformed edge map that is the edge map indicating the object at the time point t4.

Also, when an adjusted image frame is acquired as an image frame corresponding to a predetermined time point is adjusted, the controller 710 may secondarily perform image adjustment after performing image fusion on at least one of the adjusted image frames. In the following description, an example of finally acquiring an adjusted image frame corresponding to the time point t4 is described.

The controller 710 performs image fusion on the adjusted image frame 1153 corresponding to the time point t4, the adjusted image frame 1153 corresponding to the time point t3, and the adjusted image frame 1151 corresponding to the time point t2, which are at least one of the image frames acquired before or at the time point t4, and acquires a adjusted image frame (not shown) (hereinafter, referred to as the second adjusted image frame) corresponding to the time point t4 and acquired through the image fusion. The second adjusted image frame corresponding to the time point t4 is adjusted based on the edge map indicating the shape of the object at the time point t4 acquired by the operation in Block 1930, thereby acquiring a finally adjusted image frame.

Also, the controller 710 may adjust the pulse amplitude of a pulse signal based on the movement of the target object 1031 included in the object. For example, when the target object 1031 moves fast, the controller 710 may set the pulse amplitude not to decrease or to gradually decrease by decreasing a pulse amplitude decrease rate. Also, when the target object 1031 moves slowly, the controller 710 may decrease the pulse amplitude. In detail, the pulse amplitude may be set to be further decreased by setting the pulse amplitude decrease rate when the target object 1031 moves slowly to be larger or higher than the pulse amplitude decrease rate when the target object 1031 moves fast.

Figure 12:
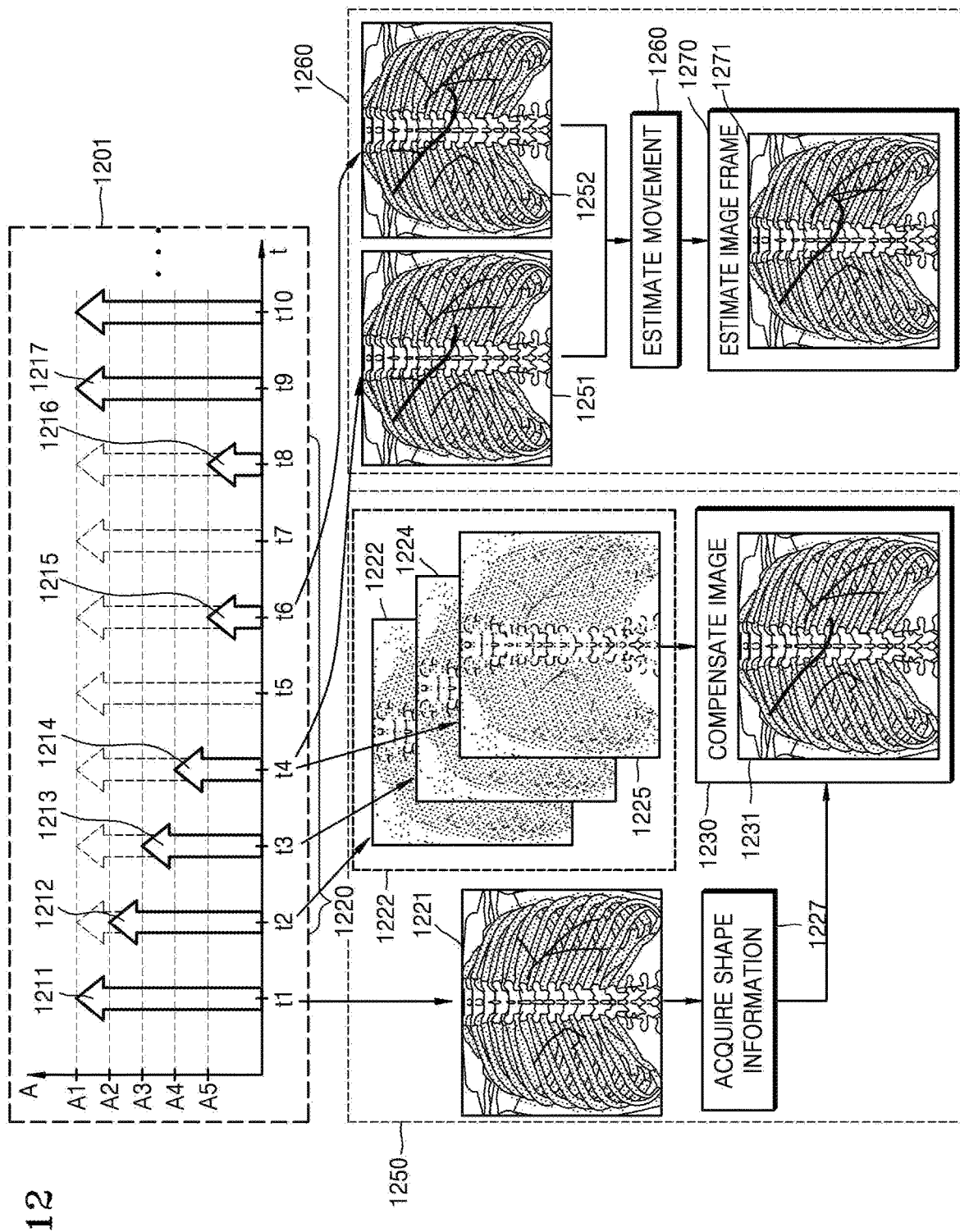
FIG. 12 is a view for describing an operation of an X-ray apparatus according to another exemplary embodiment.

FIG. 12 is a view for describing an operation of the X-ray apparatus 700 according to another exemplary embodiment.

The controller 710 may control the generation of the pulse signal 1001 in which both of the pulse rate and the pulse amplitude vary. In detail, a pulse signal 1201 includes a second section 1220 in which the pulse rate and the pulse amplitude vary, and a first section that is a time section other than the second section 1220. Also, a pulse rate of the first section may be referred to as the first pulse rate, and a pulse rate of the second section may be referred to as the second pulse rate. In FIG. 12, an example in which the second pulse rate is smaller than the first pulse rate is illustrated.

In detail, the X-ray apparatus 700 may operate as follows.

The X-ray generator 720 includes a plurality of pulses and generates a pulse type X-ray corresponding to the pulse signal 1201 in which the pulse rate and the pulse amplitude vary and radiates the generated pulse type X-ray toward the object.

The controller 710 acquires a plurality of final image frames having a frame rate larger or higher than the pulse rate of the pulse signal 1201, based on at least one reference image frame among a plurality of image frames imaged based on the pulse type X-ray.

In other words, the controller 710 performs both of the generation of the interpolated image frame descried with reference to FIG. 10 and the adjustment of the image frame described with reference to FIGS. 9B and 11, and may acquire or produce a plurality of final image frames having a frame rate larger than the pulse rate of the pulse signal 1201.

In FIG. 12, since the pulse signal 1201 identically corresponds to the pulse signal 901 of FIG. 9A, and the image frame adjustment (Operation in Block 1250) identically corresponds to the image frame adjustment (Operation in Block 945) of FIG. 9, redundant descriptions thereof are omitted. Also, in FIG. 12, since the image frame interpolation (Operation in Block 1260) identically corresponds to the image frame interpolation (Operation in Block 1070) of FIG. 10, redundant descriptions thereof are omitted.

In detail, the controller 710 performs the image frame adjustment (Operation in Block 1250) to acquire a plurality of adjusted image frames corresponding to a plurality of pulses that are actually output. The controller 710 acquires at least one interpolated image frame corresponding to at least one time point when no pulse is actually output, based on the adjusted image frames and the motion information of the object.

In detail, the controller 710 acquires an adjusted image frame 1251 corresponding to the time point t4 and an adjusted image frame 1252 corresponding to the time point t6. The adjusted image frame 1251 corresponding to the time point t4 may be the same as the adjusted image frame acquired by the above-described image frame adjustment (Operation in Block 1250).

Then, the controller 710 may generate the adjusted image frame 1251 corresponding to the time point t4 and the adjusted image frame 1252 corresponding to the time point t6, which are two adjacent adjusted image frames, and an interpolated image frame 1271 corresponding to the time point t5 based on the motion information acquired through the operation in Block 1060.

The controller 710 may generate a fluoroscopic image by using a plurality of final image frames (not shown) including at least one interpolated image frame 1271 and a plurality of corrected image frames, for example, a corrected image frame 1231, corresponding to a plurality of pulses that are actually output.

Also, the controller 710 may adjust the pulse amplitude and pulse rate of the pulse signal 1201 based on the movement of the target object 1031 included in the object.

Also, the image frames described with reference to FIGS. 8 to 12 may be image frames acquired by imaging the FOV (field of view). Accordingly, the controller 710 may adjust at least one of the image frames acquired by imaging FOV.

Also, the image frames described with reference to FIGS. 8 to 12 may be image frames acquired by imaging a non-region of interest (non-ROI). Accordingly, the controller 710 may adjust at least one of the image frames acquired by imaging the non-ROI.

Also, the image frames described with reference to FIGS. 8 to 12 may be image frames acquired by imaging an ROI. Accordingly, the controller 710 may adjust at least one of the image frames acquired by imaging the ROI.

Also, the X-ray apparatus 700 may generate an interpolated image frame indicating or for the FOV or the non-ROI. Since the ROI is a portion of the object that the user importantly observes, an image frame imaged by outputting an actual pulse may be used to increase accuracy of an image without using the interpolated image frame. Accordingly, the interpolated image frame may be generated for the FOV or the non-ROI, and the image frame imaged by outputting an actual pulse may be used for the ROI.

Also, the controller 710 may selectively perform at least one of the above-described image frame correction and the above-described image frame interpolation on at least one of the ROI, the non-ROI, and the FOV. For example, when one image frame includes both of the ROI and the non-ROI, the controller 710 may perform only the above-described image frame correction on the ROI and the above-described image frame interpolation on the ROI. Also, the user may select at least one region, for example, the ROI, the non-ROI, and the FOV, to perform the adjustment through the user interface 735.

Figure 13:
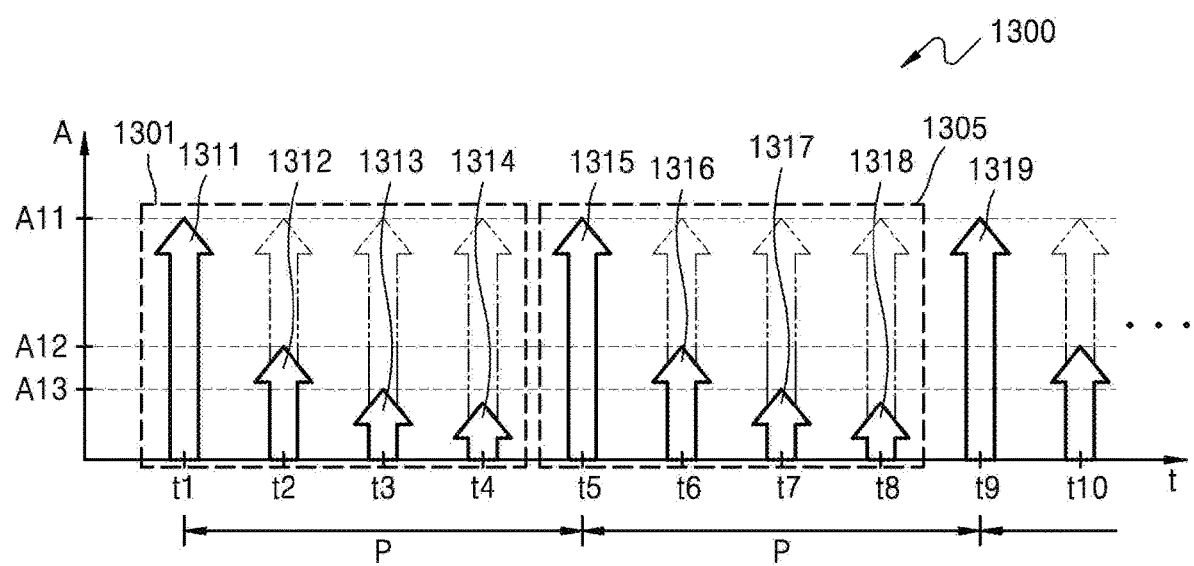
FIG. 13 is a view for describing an operation of an X-ray apparatus according to another exemplary embodiment.

FIG. 13 is a view for describing an operation of the X-ray apparatus 700 according to another exemplary embodiment.

Also, the X-ray apparatus 700 operates as follows.

The controller 710 controls generation of a pulse signal in which a plurality of pulses, included in one cycle, have a predetermined pattern. The pulses included in one cycle of a pulse signal include at least two different pulses. Also, the controller 710 controls generation of a pulse type X-ray corresponding to the pulse signal.

The X-ray generator 720 generates the pulse type X-ray.

Referring to FIG. 13, in a pulse signal 1300, a plurality of pulses 1311, 1312, 1313, and 1314 included in one cycle P have a predetermined pattern 1301. Also, a plurality of pulses 1315, 1316, 1317, and 1318 included in subsequent one cycle P have a predetermined pattern 1305 like the predetermined pattern 1301. At least two pulses 1311, 1312, 1313, and 1314 included in one cycle P are different from each other.

In detail, in the at least two of the pulses included in one cycle P, at least one of the pulse rate and the pulse amplitude may be different from each other. In FIG. 13, an example in which each of the pulses 1311, 1312, 1313, and 1314, included in one cycle P, has a different pulse amplitude is illustrated.

Also, the predetermined pattern 1301, for example, may be set based on the movement of at least one of the object and the target object 1031.

For example, when the target object 1031 moves fast, as in the case of moving through the relatively thick blood vessel as described above, the pulse amplitude may be gradually decreased or may not be decreased. Also, the target object 1031 moves slowly as in the case of moving through the relatively thin blood vessel, a decrease rate of the pulse amplitude may be increased or the pulse rate may be decreased.

Also, a detailed shape of the predetermined pattern 1301 may be set to be experimentally optimized. For example, the predetermined pattern 1301 may be set to be different according to a moving portion of the target object 1031, taking into consideration a desired quality of an X-ray image, so as to meet a desired image quality.

Also, the predetermined pattern 1301 may be set based on a user input through the user interface 735. The user may input pattern setting information to set the predetermined pattern 1301 to be different through the user interface 735 according to the moving portion of the target object 1031 or the movement of the target object 1031.

Figure 14:
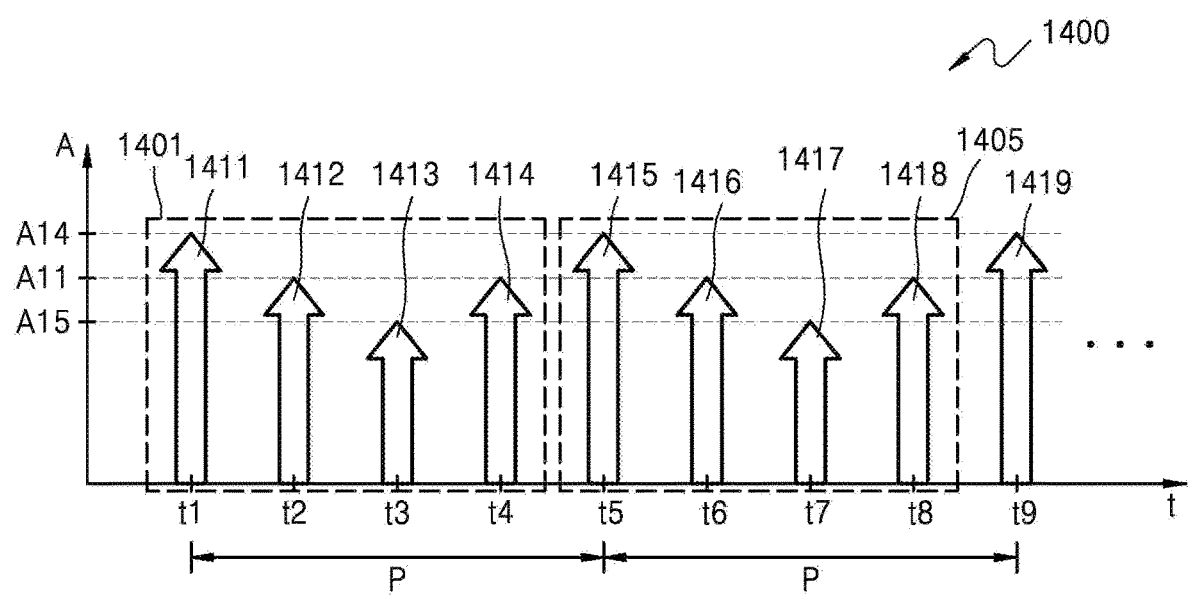
FIG. 14 is a view for describing an operation of an X-ray apparatus according to another exemplary embodiment.

FIG. 14 is a view for describing an operation of the X-ray apparatus 700 according to another exemplary embodiment.

Referring to FIG. 14, a pulse signal 1400 including a pattern, for example, a pattern 1401, which is different from the pattern 1301 of FIG. 13, is illustrated. In the pulse signal 1400, a plurality of pulses 1411, 1412, 1413, and 1414 included in one cycle P have the predetermined pattern 1401.

In detail, in the predetermined pattern 1301 of FIG. 13, the maximum amplitude value is A11 and the minimum amplitude value is A13, in which a relationship that A11>A12>A13 is established. In a pattern illustrated in FIG. 14, the maximum amplitude value is A14 and the minimum amplitude value is A15, in which relationships that A14>A11 and A15>A13 are established.

The controller 710 may adaptively set the pattern of a pulse signal based on the movement of at least one of the object and the target object 1031, as described above. In detail, when the speed of the target object 1031 moving through the first portion is slower than through the second portion, the pulse signal may be generated to have the predetermined pattern 1301 of FIG. 13 when moving through the first portion, and to have the pattern 1401 in which the pulse amplitude increases as a whole compared to the predetermined pattern 1301 as illustrated in FIG. 15 when the pulse signal moves through the second portion.

Figure 15:
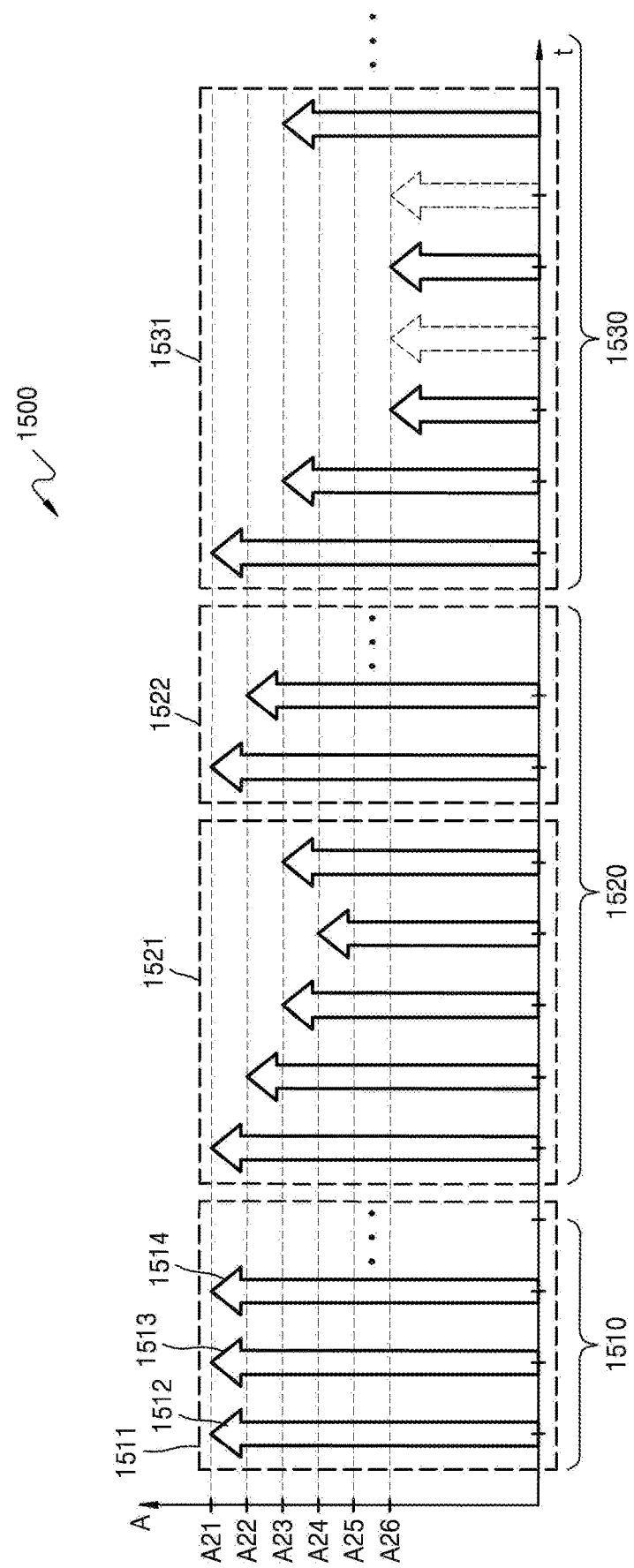
FIG. 15 is a view for describing a pulse signal having at least one predetermined pattern.

FIG. 15 is a view for describing a pulse signal having at least one predetermined pattern.

The controller 710 may control generation of the pulse type X-ray corresponding to a pulse signal having at least two predetermined patterns. Each of the at least two predetermined patterns includes at least two different pulses of a plurality of pulses included in one cycle. The X-ray generator 720 generates a pulse type X-ray according to the control of the controller 710.

Referring to FIG. 15, the controller 710 may control generation of a pulse signal having at least two predetermined patterns 1511, 1521, and 1531. The predetermined pattern includes at least two pulses in which at least one of the pulse rate and the pulse amplitude is different as described with reference to FIGS. 13 and 14. In detail, the controller 710 may adaptively change the pattern included in the pulse signal based on the movement of the target object 1031.

For example, the controller 710 generates a pulse signal having a pattern 1511 in which the pulse amplitude and the pulse rate are the maximum for the object portion where the target object 1031 moves fast. In detail, the controller 710 may cyclically generate a plurality of pulses 1512, 1513, and 1514 having the pattern 1511 in a first time section 1510 in which the target object 1031 moves fast, and may generate a plurality of pulses having a pattern 1521 by decreasing the pulse amplitude in a second time section 1520 in which the target object 1031 moves slower than in the first time section 1510. The controller 710 may generate a plurality of pulses having a pattern 1531 by decreasing the pulse amplitude and the pulse rate in a third time section 1530 in which the target object 1031 moves slower than in the second time section 1520.

The controller 710 may control generation of a pulse type X-ray corresponding to a pulse signal having at least two predetermined patterns by setting at least two predetermined patterns based on the movement of at least one of the object and the target object 1031.

Figure 16:
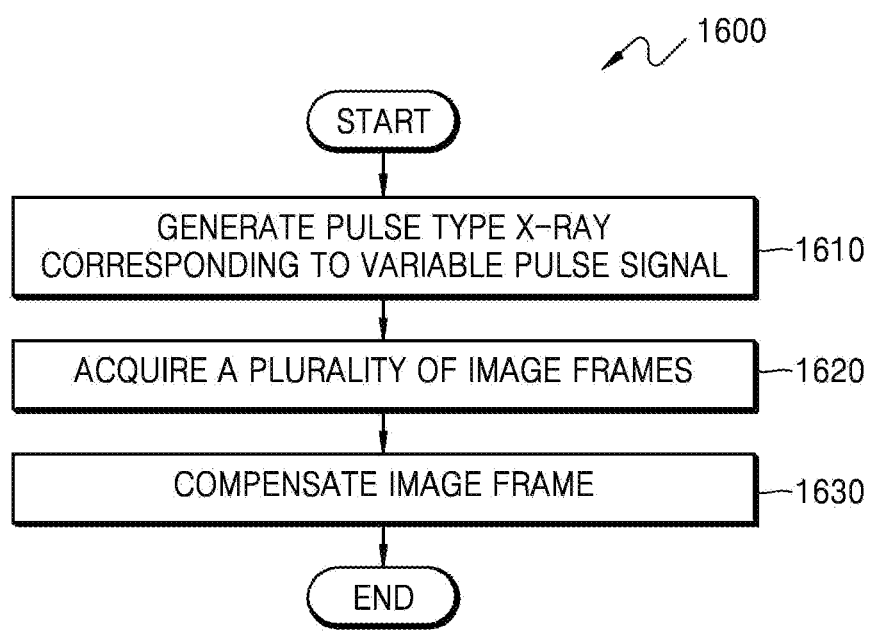
FIG. 16 is a flowchart for explaining an X-ray imaging method according to an exemplary embodiment.

FIG. 16 is a flowchart for explaining an X-ray imaging method 1600 according to an exemplary embodiment. The X-ray imaging method 1600 according to the present exemplary embodiment has the same structural characteristics as the X-ray apparatuses 600 and 700 described with reference to FIGS. 1 to 15. Accordingly, in the description of the X-ray imaging method 1600, redundant descriptions thereof with respect to FIGS. 1 to 15 are omitted. Also, the X-ray imaging method 1600 is described with reference to the X-ray apparatus 700 of FIG. 7.

The X-ray apparatus 700 generates a pulse type X-ray corresponding to a pulse signal including a plurality of pulses in which at least one of the pulse rate and the pulse amplitude varies (Operation 1610). The operation 1610 may be performed by the X-ray generator 720 according to the control of the controller 710. In detail, the controller 710 may adjust at least one of the pulse rate and the pulse amplitude based on the movement of the object. In detail, the controller 710 may adjust at least one of the pulse rate and the pulse amplitude of a pulse signal based on the target object 1031 included in the object. In detail, at least one of the pulse rate and the pulse amplitude of a pulse signal may be adjusted based on the movement speed of the target object 1031.

A plurality of image frames are acquired by using the pulse type X-ray passing through the object (Operation 1620). The operation 1620 may be performed by the controller 710. In detail, in the operation 1620, shape information indicating the object at at least one time point is acquired, and at least one of the image frames may be adjusted based on the acquired shape information. The shape information may include at least one of a feature map indicating the shape of the object and an edge map indicating a surface included in the object.

At least one adjusted image frame is acquired by adjusting at least one of the image frames acquired in the operation 1620 (Operation 1630). The operation 1630 may be performed by the controller 710.

Also, in the X-ray imaging method 1600 may generate at least one interpolated image frame located between the image frames may be generated based on at least one of the image frames (Operation not shown). The operation of generating an interpolated image frame may be performed after the operation 1620.

Also, the X-ray imaging method 1600 further includes generating of a fluoroscopy X-ray image based on the adjusted image frames (Operation not shown). In the X-ray imaging method 1600, the fluoroscopy X-ray image may be generated based on at least one of the interpolated image frame and the adjusted image frames.

Also, in the X-ray imaging method 1600, the fluoroscopy X-ray image may be displayed (Operation not shown).

Figure 17:
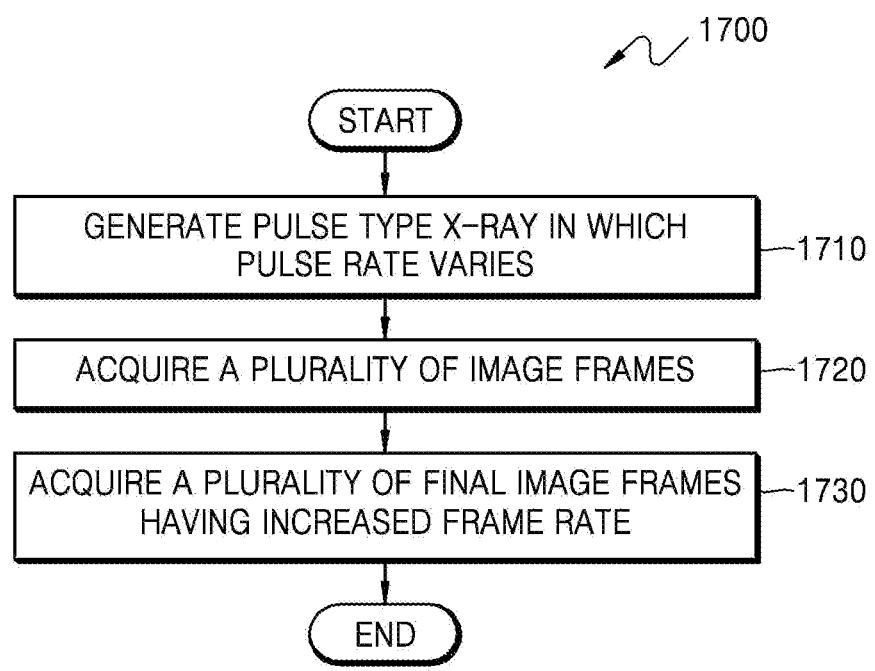
FIG. 17 is a flowchart for explaining an X-ray imaging method according to another exemplary embodiment.

FIG. 17 is a flowchart for explaining an X-ray imaging method 1700 according to another exemplary embodiment. The X-ray imaging method 1700 according to the present exemplary embodiment has the same structural characteristics as the X-ray apparatuses 600 and 700 described with reference to FIGS. 1 to 15. Accordingly, in the description of the X-ray imaging method 1600, redundant descriptions thereof with respect to FIGS. 1 to 15 are omitted. Also, the X-ray imaging method 1700 is described with reference to the X-ray apparatus 700 of FIG. 7.

A pulse type X-ray having a plurality of pulses including and corresponding to a pulse signal in which the pulse rate varies is generated (Operation 1710). The operation 1710 may be performed by the X-ray generator 720 according to the control of the controller 710.

A plurality of image frames are acquired based on the pulse type X-ray radiated toward the object (Operation 1720). The operation 1620 may be performed by the controller 710.

A plurality of final image frames having a frame rate larger or higher than the pulse rate of the pulse signal are acquired or produced based on the image frames acquired in the operation 1720 (Operation 1730). The operation 1730 may be performed by the controller 710. In detail, the operation 1730 may include acquiring information about the movement of the object and generating at least one interpolated image frame based on the acquired information and at least one of the image frames, and acquiring or producing a plurality of final image frames including the at least one interpolated image frame.

Figure 18:
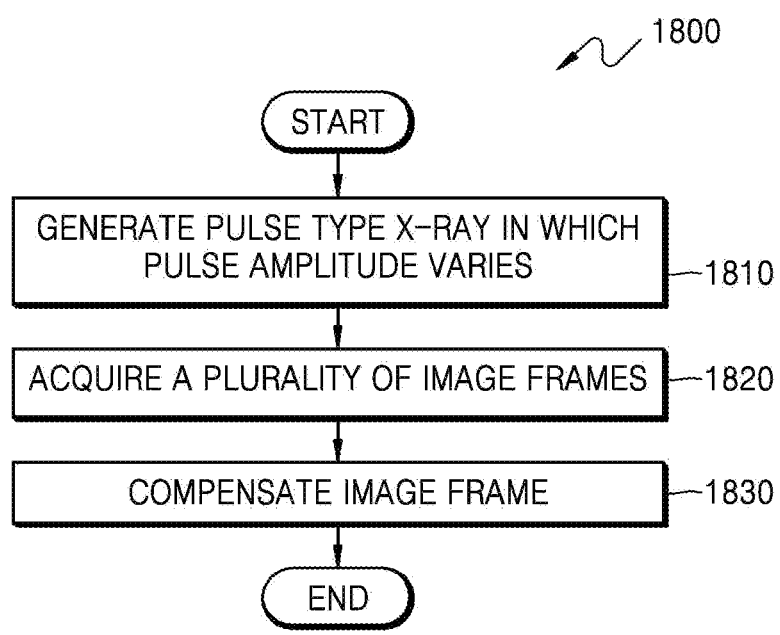
FIG. 18 is a flowchart for explaining an X-ray imaging method according to another exemplary embodiment.

FIG. 18 is a flowchart for explaining an X-ray imaging method 1800 according to another exemplary embodiment. The X-ray imaging method 1800 according to the present exemplary embodiment has the same structural characteristics as the X-ray apparatuses 600 and 700 described with reference to FIGS. 1 to 15. Accordingly, in the description of the X-ray imaging method 1800, redundant descriptions thereof with respect to FIGS. 1 to 15 are omitted. Also, the X-ray imaging method 1800 is described with reference to the X-ray apparatus 700 of FIG. 7.

A pulse type X-ray including a plurality of pulses and corresponding to a pulse signal in which the pulse amplitude varies is generated (Operation 1810). The operation 1810 may be performed by the X-ray generator 720 according to the control of the controller 710.

A plurality of image frames are acquired based on the pulse type X-ray radiated toward the object (Operation 1820). The operation 1820 may be performed by the controller 710.

At least one adjusted image frame among a plurality of image frames is adjusted based on at least one reference image frame of the image frames (Operation 1830). The operation 1830 may be performed by the controller 710. In detail, in the operation 1830, shape information indicating the object at at least one time point based on at least one reference image frame, and at least one of the image frames may be adjusted based on the shape information.

Figure 19:
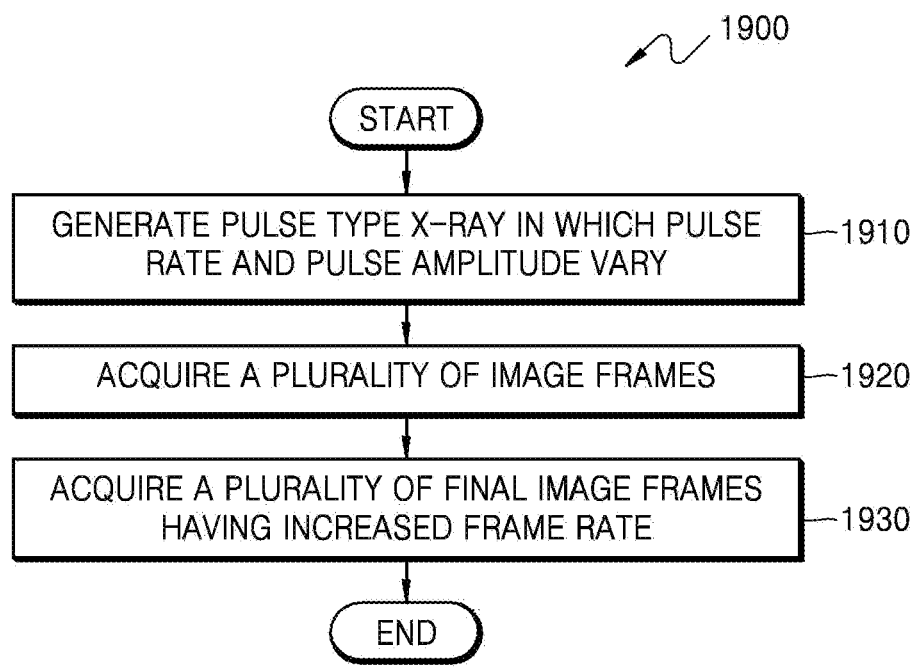
FIG. 19 is a flowchart for explaining an X-ray imaging method according to another exemplary embodiment.

FIG. 19 is a flowchart for explaining an X-ray imaging method 1900 according to another exemplary embodiment. The X-ray imaging method 1900 according to the present exemplary embodiment has the same structural characteristics as the X-ray apparatuses 600 and 700 described with reference to FIGS. 1 to 15. Accordingly, in the description of the X-ray imaging method 1900, redundant descriptions thereof with respect to FIGS. 1 to 15 are omitted. Also, the X-ray imaging method 1900 is described with reference to the X-ray apparatus 700 of FIG. 7.

A pulse type X-ray including a plurality of pulses and corresponding to a pulse signal in which the pulse rate and the pulse amplitude vary is generated (Operation 1910). The operation 1910 may be performed by the X-ray generator 720 according to the control of the controller 710.

A plurality of image frames are acquired based on the pulse type X-ray radiated toward the object (Operation 1920). The operation 1920 may be performed by the controller 710.

A plurality of final image frames having a frame rate larger than the pulse rate of the pulse signal is acquired based on at least one reference image frame of the image frames (Operation 1930). The operation 1930 may be performed by the controller 710. In detail, the operation 1930 may include generating at least one interpolated image frame based on information about the movement of the object, and acquiring a plurality of final image frames including the at least one interpolated image frame. Alternatively, the operation 1930 may include generating at least one reference image frame by adjusting at least one of image frame of the image frames, and acquiring a plurality of final image frames including the at least one adjusted image frame.

Figure 20:
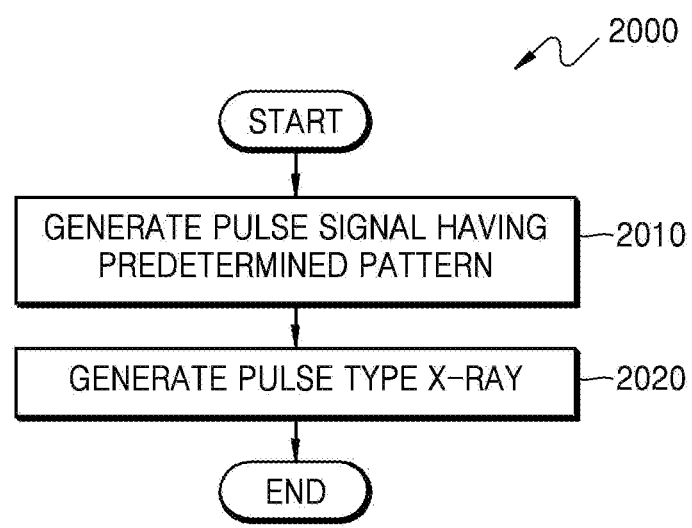
FIG. 20 is a flowchart for explaining an X-ray imaging method according to another exemplary embodiment.

FIG. 20 is a flowchart for explaining an X-ray imaging method 2000 according to another exemplary embodiment. The X-ray imaging method 2000 according to the present exemplary embodiment has the same structural characteristics as the X-ray apparatuses 600 and 700 described with reference to FIGS. 1 to 15. Accordingly, in the description of the X-ray imaging method 2000, redundant descriptions thereof with respect to FIGS. 1 to 15 are omitted. Also, the X-ray imaging method 2000 is described with reference to the X-ray apparatus 700 of FIG. 7.

A pulse signal is generated in which a plurality of pulses included in one cycle have a predetermined pattern and which includes at least two different pulses of the pulses included in one cycle (Operation 2010). The operation 2010 may be performed by the controller 710. In detail, in at least two of the pulses included in one cycle, at least one of the pulse rate and the pulse amplitude is different.

A pulse type X-ray corresponding to the pulse signal is generated (Operation 2020). The operation 2020 may be performed by the X-ray generator 720 according to the controller 710.

As described above, in the X-ray apparatus and the X-ray imaging method according to the one or more of the above embodiments, a variable pulse is generated and used to adjust at least one of the pulse rate and the pulse amplitude. Accordingly, in the X-ray apparatus and an X-ray imaging method according to the one or more of the above embodiments, the amount of radiation radiated toward the object may be decreased, and thus a low radiation amount of X-ray imaging may be embodied. Also, since the variable pulse is flexibly adjusted based on the movement of the object and the target object 1031, an amount of radiation is reduced and a natural fluoroscopic image may be provided.

Also, in the X-ray apparatus and an X-ray imaging method according to the one or more of the above embodiments, a variable pulse is generated and used to adjust at least one of the pulse rate and the pulse amplitude, a plurality of image frames to be imaged are adjusted or interpolated. Accordingly, even when the amount of radiation is reduced, due to the image frame adjustment or interpolation, an X-ray image having no deterioration in the quality of an image may be generated and provided.

In addition, other embodiments can also be implemented through computer readable code/instructions in/on a non-transitory medium, e.g., a computer readable medium, to control at least one processing element to implement any above described embodiment. The medium can correspond to any medium/media permitting the storage and/or transmission of the computer readable code.

Examples of the computer-readable recording medium include magnetic storage media (e.g., ROM, floppy disks, hard disks, etc.), optical recording media (e.g., CD-ROMs, or DVDs), etc.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An X-ray apparatus, comprising:
   an X-ray generator to generate the X-ray; and
   a controller configured to:
      control the X-ray generator to generate the X-ray corresponding to a pulse signal including a plurality of pulses;
      control at least one of a pulse rate and a pulse amplitude of the plurality of pulses included in the pulse signal based on a motion of at least one of an object and a target object included in the object, the pulse signal comprising
         a first section including at least one of the plurality of pulses, and
         a second section including at least one of the plurality of pulses; and
      adjust at least one of a plurality of image frames corresponding to the at least one of the plurality of pulses included in the second section based on an image frame which is among the plurality of image frames and corresponds to at least one reference pulse among the plurality of pulses included in the first section.

2. The X-ray apparatus of claim 1, wherein the controller adjusts at least one of the plurality of image frames based on at least one of the plurality of image frames corresponding to the at least one of the plurality of pulses.

3. The X-ray apparatus of claim 1, wherein respective pulse rates of the plurality of pulses included in the second section are equal to or less than a pulse rate of at least one of the plurality of pulses included in the first section, and respective pulse amplitudes of the plurality of pulses included in the second section are equal to or less than a pulse amplitude of at least one of the plurality of pulses included in the first section.

4. The X-ray apparatus of claim 1, wherein
   the first section of the pulse signal comprises at least one of the plurality of pulses that are applied while a target object moves through a first portion of the object,
   the second section of the pulse signal comprises at least one of the plurality of pulses that are applied while the target object moves through a second portion of the object, and
   the target object moves slower in the second portion than in the first portion.

5. The X-ray apparatus of claim 4, wherein the first portion is a first region of the object including a first blood vessel, and the second portion is a second region of the object including a second blood vessel which is thinner than the first blood vessel.

6. The X-ray apparatus of claim 1, wherein,
   the at least one reference pulse includes a reference pulse,
   the plurality of pulses included in the second section includes a first pulse adjacent to the reference pulse and has an amplitude smaller than the amplitude of the reference pulse, and
   the controller generates an adjusted first image frame by adjusting a first image frame corresponding to the first pulse based on a reference image frame corresponding to the reference pulse.

7. The X-ray apparatus of claim 1, wherein the controller adjusts the at least one of the plurality of image frames each representing at least one of a field of view (FOV), a non-region of interest (non-ROI) and a region of interest (ROI).

8. The X-ray apparatus of claim 1, wherein the controller generates a fluoroscopy X-ray image based on the at least one adjusted image frame.

* * * * *